United States Patent
McCombie et al.

(10) Patent No.: US 10,357,187 B2
(45) Date of Patent: Jul. 23, 2019

(54) OPTICAL SENSOR FOR MEASURING PHYSIOLOGICAL PROPERTIES

(75) Inventors: Devin McCombie, San Diego, CA (US); Gunnar Trommer, Encinitas, CA (US); Jim Moon, Portland, OR (US); Marshall Dhillon, San Diego, CA (US); Scott Clear, Escondido, CA (US); Julian Groeli, San Diego, CA (US)

(73) Assignee: SOTERA WIRELESS, INC., San Diego, CA (US)

( * ) Notice: Subject to any disclaimer, the term of this patent is extended or adjusted under 35 U.S.C. 154(b) by 1579 days.

(21) Appl. No.: 13/399,586

(22) Filed: Feb. 17, 2012

(65) Prior Publication Data

US 2013/0046159 A1 Feb. 21, 2013

Related U.S. Application Data

(60) Provisional application No. 61/444,320, filed on Feb. 18, 2011.

(51) Int. Cl.
*A61B 5/1455* (2006.01)
*A61B 5/00* (2006.01)

(52) U.S. Cl.
CPC ........ *A61B 5/14552* (2013.01); *A61B 5/6826* (2013.01)

(58) Field of Classification Search
CPC .. A61B 5/1455; A61B 5/14552; A61B 5/6826
USPC .................................................. 600/309–344
See application file for complete search history.

(56) References Cited

U.S. PATENT DOCUMENTS

| | | |
|---|---|---|
| 4,263,918 A | 4/1981 | Swearingen et al. |
| 4,270,547 A | 6/1981 | Steffen et al. |
| 4,305,400 A | 12/1981 | Logan |
| 4,367,752 A | 1/1983 | Jimenez et al. |
| 4,577,639 A | 3/1986 | Simon et al. |
| 4,582,068 A | 4/1986 | Phillipps et al. |
| 4,653,498 A | 3/1987 | New, Jr. et al. |

(Continued)

FOREIGN PATENT DOCUMENTS

| | | |
|---|---|---|
| EP | 0443267 A1 | 8/1991 |
| EP | 0993803 A1 | 4/2000 |

(Continued)

OTHER PUBLICATIONS

Non-Final Office Action issued by the US Patent and Trademark Office dated Aug. 31, 2012 in U.S. Appl. No. 12/469,213.

(Continued)

*Primary Examiner* — Eric F Winakur
*Assistant Examiner* — Marjan Fardanesh
(74) *Attorney, Agent, or Firm* — Acuity Law Group, PC; Michael A. Whittaker

(57) ABSTRACT

The invention provides a physiological probe that comfortably attaches to the base of the patient's thumb, thereby freeing up their fingers for conventional activities in a hospital, such as reading and eating. The probe, which comprises a separate cradle module and sensor module, secures to the thumb and measures time-dependent signals corresponding to LEDs operating near 660 and 905 nm. The cradle module, which contains elements subject to wear, is preferably provided as a disposable unit.

14 Claims, 7 Drawing Sheets

(56) References Cited

U.S. PATENT DOCUMENTS

| | | | |
|---|---|---|---|
| 4,710,164 A | 12/1987 | Levin et al. |
| 4,722,351 A | 2/1988 | Phillipps et al. |
| 4,802,486 A | 2/1989 | Goodman et al. |
| 4,807,638 A | 2/1989 | Sramek |
| 4,905,697 A | 3/1990 | Heggs et al. |
| 5,025,791 A | 6/1991 | Niwa |
| 5,140,990 A | 8/1992 | Jones et al. |
| 5,190,038 A | 3/1993 | Polson et al. |
| 5,197,489 A | 3/1993 | Conlan |
| 5,247,931 A | 9/1993 | Norwood |
| 5,316,008 A | 5/1994 | Suga et al. |
| 5,339,818 A | 8/1994 | Baker et al. |
| 5,435,315 A | 7/1995 | McPhee et al. |
| 5,448,991 A | 9/1995 | Polson et al. |
| 5,465,082 A | 11/1995 | Chaco |
| 5,482,036 A | 1/1996 | Diab et al. |
| 5,485,838 A | 1/1996 | Ukawa et al. |
| 5,490,505 A | 2/1996 | Diab et al. |
| 5,515,858 A | 5/1996 | Myllymaki |
| 5,517,988 A | 5/1996 | Gerhard |
| 5,524,637 A | 6/1996 | Erickson |
| 5,549,650 A | 8/1996 | Bornzin et al. |
| 5,575,284 A | 11/1996 | Athan et al. |
| 5,577,508 A | 11/1996 | Medero |
| 5,588,427 A | 12/1996 | Tien |
| 5,593,431 A | 1/1997 | Sheldon |
| 5,632,272 A | 5/1997 | Diab et al. |
| 5,649,543 A | 7/1997 | Hosaka et al. |
| 5,680,870 A | 10/1997 | Hood et al. |
| 5,685,299 A | 11/1997 | Diab et al. |
| 5,709,205 A | 1/1998 | Bukta |
| 5,743,856 A | 4/1998 | Oka et al. |
| 5,766,131 A | 6/1998 | Kondo et al. |
| 5,769,785 A | 6/1998 | Diab et al. |
| 5,800,349 A | 9/1998 | Isaacson et al. |
| 5,820,550 A | 10/1998 | Polson et al. |
| 5,848,373 A | 12/1998 | Delorme et al. |
| 5,853,370 A | 12/1998 | Chance et al. |
| 5,857,975 A | 1/1999 | Golub |
| 5,865,755 A | 2/1999 | Golub |
| 5,865,756 A | 2/1999 | Peel, III |
| 5,873,834 A | 2/1999 | Yanagi et al. |
| 5,876,353 A | 3/1999 | Riff |
| 5,895,359 A | 4/1999 | Peel, III |
| 5,899,855 A | 5/1999 | Brown |
| 5,913,827 A | 6/1999 | Gorman |
| 5,919,141 A | 7/1999 | Money et al. |
| 5,941,836 A | 8/1999 | Friedman |
| 5,964,701 A | 10/1999 | Asada et al. |
| 5,964,720 A | 10/1999 | Pelz |
| 5,971,930 A | 10/1999 | Elghazzawi |
| 6,002,952 A | 12/1999 | Diab et al. |
| 6,011,985 A | 1/2000 | Athan et al. |
| 6,018,673 A | 1/2000 | Chin et al. |
| 6,036,642 A | 3/2000 | Diab et al. |
| 6,041,783 A | 3/2000 | Gruenke |
| 6,057,758 A | 5/2000 | Dempsey et al. |
| 6,067,462 A | 5/2000 | Diab et al. |
| 6,081,735 A | 6/2000 | Diab et al. |
| 6,081,742 A | 6/2000 | Amano et al. |
| 6,094,592 A | 7/2000 | Yorkey et al. |
| 6,117,077 A | 9/2000 | Del Mar et al. |
| 6,129,686 A | 10/2000 | Friedman |
| 6,157,850 A | 12/2000 | Diab et al. |
| 6,159,147 A | 12/2000 | Lichter et al. |
| 6,160,478 A | 12/2000 | Jacobsen et al. |
| 6,168,569 B1 | 1/2001 | McEwen et al. |
| 6,176,831 B1 | 1/2001 | Voss et al. |
| 6,198,394 B1 | 3/2001 | Jacobsen et al. |
| 6,198,951 B1 | 3/2001 | Kosuda et al. |
| 6,199,550 B1 | 3/2001 | Wiesmann et al. |
| 6,206,830 B1 | 3/2001 | Diab et al. |
| 6,236,872 B1 | 5/2001 | Diab et al. |
| 6,251,080 B1 | 6/2001 | Henkin et al. |
| 6,261,247 B1 | 7/2001 | Ishikawa et al. |
| 6,262,769 B1 | 7/2001 | Anderson et al. |
| 6,263,222 B1 | 7/2001 | Diab et al. |
| 6,287,262 B1 | 9/2001 | Amano et al. |
| 6,322,516 B1 | 11/2001 | Masuda et al. |
| 6,334,065 B1 | 12/2001 | Al-Ali et al. |
| 6,371,921 B1 | 4/2002 | Caro et al. |
| 6,388,240 B2 | 5/2002 | Schulz et al. |
| RE37,852 E | 9/2002 | Aso et al. |
| 6,443,890 B1 | 9/2002 | Schulze et al. |
| 6,480,729 B2 | 11/2002 | Stone |
| 6,491,647 B1 | 12/2002 | Bridger et al. |
| 6,503,206 B1 | 1/2003 | Li et al. |
| 6,514,218 B2 | 2/2003 | Yamamoto |
| 6,516,289 B2 | 2/2003 | David |
| 6,526,310 B1 | 2/2003 | Carter et al. |
| 6,527,729 B1 | 3/2003 | Turcott |
| 6,541,756 B2 | 4/2003 | Schulz et al. |
| 6,544,173 B2 | 4/2003 | West et al. |
| 6,544,174 B2 | 4/2003 | West et al. |
| 6,546,267 B1 | 4/2003 | Sugiura et al. |
| 6,551,252 B2 | 4/2003 | Sackner et al. |
| 6,584,336 B1 | 6/2003 | Ali et al. |
| 6,589,170 B1 | 7/2003 | Flach et al. |
| 6,595,929 B2 | 7/2003 | Stivoric et al. |
| 6,605,038 B1 | 8/2003 | Teller et al. |
| 6,606,993 B1 | 8/2003 | Wiesmann et al. |
| 6,616,606 B1 | 9/2003 | Petersen et al. |
| 6,645,154 B2 | 11/2003 | Oka |
| 6,650,917 B2 | 11/2003 | Diab et al. |
| 6,684,090 B2 | 1/2004 | Ali et al. |
| 6,694,177 B2 | 2/2004 | Eggers et al. |
| 6,699,194 B1 | 3/2004 | Diab et al. |
| 6,732,064 B1 | 5/2004 | Kadtke et al. |
| 6,745,060 B2 | 6/2004 | Diab et al. |
| 6,770,028 B1 | 8/2004 | Ali et al. |
| 6,790,178 B1 | 9/2004 | Mault et al. |
| 6,811,538 B2 | 11/2004 | Westbrook et al. |
| 6,845,256 B2 | 1/2005 | Chin et al. |
| 6,850,787 B2 | 2/2005 | Weber et al. |
| 6,879,850 B2 | 4/2005 | Kimball |
| 6,893,396 B2 | 5/2005 | Schulze et al. |
| 6,912,414 B2 | 6/2005 | Tong |
| 6,934,571 B2 | 8/2005 | Wiesmann et al. |
| 6,947,781 B2 | 9/2005 | Asada et al. |
| 6,976,958 B2 | 12/2005 | Quy |
| 6,985,078 B2 | 1/2006 | Suzuki et al. |
| 6,997,882 B1 | 2/2006 | Parker et al. |
| 7,020,508 B2 | 3/2006 | Stivoric et al. |
| 7,020,578 B2 | 3/2006 | Sorensen et al. |
| 7,029,447 B2 | 4/2006 | Rantala |
| 7,041,060 B2 | 5/2006 | Flaherty et al. |
| 7,048,687 B1 | 5/2006 | Reuss et al. |
| 7,115,824 B2 | 10/2006 | Lo |
| 7,156,809 B2 | 1/2007 | Quy |
| 7,184,809 B1 | 2/2007 | Sterling et al. |
| 7,186,966 B2 | 3/2007 | Al-Ali |
| 7,194,293 B2 | 3/2007 | Baker, Jr. |
| 7,215,984 B2 | 5/2007 | Diab et al. |
| 7,215,987 B1 | 5/2007 | Sterling et al. |
| 7,225,007 B2 | 5/2007 | Al-Ali et al. |
| 7,237,446 B2 | 7/2007 | Chan et al. |
| 7,241,265 B2 | 7/2007 | Cummings et al. |
| 7,257,438 B2 | 8/2007 | Kinast |
| 7,296,312 B2 | 11/2007 | Menkedick et al. |
| 7,299,159 B2 | 11/2007 | Nanikashvili |
| 7,301,451 B2 | 11/2007 | Hastings |
| 7,314,451 B2 | 1/2008 | Halperin et al. |
| 7,351,206 B2 | 4/2008 | Suzuki et al. |
| 7,355,512 B1 | 4/2008 | Al-Ali |
| 7,373,191 B2 | 5/2008 | Delonzer et al. |
| 7,373,912 B2 | 5/2008 | Self et al. |
| 7,377,794 B2 | 5/2008 | Al-Ali et al. |
| 7,382,247 B2 | 6/2008 | Welch et al. |
| 7,383,069 B2 | 6/2008 | Ruchti et al. |
| 7,383,070 B2 | 6/2008 | Diab et al. |
| 7,384,398 B2 | 6/2008 | Gagnadre et al. |
| 7,400,919 B2 | 7/2008 | Petersen et al. |
| 7,412,272 B2 * | 8/2008 | Medina ............... 600/344 |
| 7,420,472 B2 | 9/2008 | Tran |

(56) References Cited

U.S. PATENT DOCUMENTS

| | | |
|---|---|---|
| 7,427,926 B2 | 9/2008 | Sinclair et al. |
| 7,455,643 B1 | 11/2008 | Li et al. |
| 7,468,036 B1 | 12/2008 | Rulkov et al. |
| 7,477,143 B2 | 1/2009 | Albert |
| 7,479,890 B2 | 1/2009 | Lehrman et al. |
| 7,485,095 B2 | 2/2009 | Shusterman |
| 7,502,643 B2 | 3/2009 | Farringdon et al. |
| 7,508,307 B2 | 3/2009 | Albert |
| 7,509,131 B2 | 3/2009 | Krumm et al. |
| 7,509,154 B2 | 3/2009 | Diab et al. |
| 7,522,035 B2 | 4/2009 | Albert |
| 7,530,949 B2 | 5/2009 | Al-Ali et al. |
| 7,539,532 B2 | 5/2009 | Tran |
| 7,541,939 B2 | 6/2009 | Zadesky et al. |
| 7,542,878 B2 | 6/2009 | Nanikashvili |
| 7,586,418 B2 | 9/2009 | Cuddihy et al. |
| 7,598,878 B2 | 10/2009 | Goldreich |
| 7,602,301 B1 | 10/2009 | Stirling et al. |
| 7,616,110 B2 | 11/2009 | Crump et al. |
| 7,625,344 B1 | 12/2009 | Brady et al. |
| 7,628,071 B2 | 12/2009 | Sasaki et al. |
| 7,628,730 B1 | 12/2009 | Watterson et al. |
| 7,641,614 B2 | 1/2010 | Asada et al. |
| 7,648,463 B1 | 1/2010 | Elhag et al. |
| 7,656,287 B2 | 2/2010 | Albert et al. |
| 7,668,588 B2 | 2/2010 | Kovacs |
| 7,670,295 B2 | 3/2010 | Sackner et al. |
| 7,674,230 B2 | 3/2010 | Reisfeld |
| 7,674,231 B2 | 3/2010 | McCombie et al. |
| 7,678,061 B2 | 3/2010 | Lee et al. |
| 7,684,954 B2 | 3/2010 | Shahabdeen et al. |
| 7,689,437 B1 | 3/2010 | Teller et al. |
| 7,698,101 B2 | 4/2010 | Alten et al. |
| 7,698,830 B2 | 4/2010 | Townsend et al. |
| 7,698,941 B2 | 4/2010 | Sasaki et al. |
| 7,715,984 B2 | 5/2010 | Ramakrishnan et al. |
| 7,725,147 B2 | 5/2010 | Li et al. |
| 7,782,189 B2 | 8/2010 | Spoonhower et al. |
| 7,827,011 B2 | 11/2010 | Devaul et al. |
| 7,925,022 B2 | 4/2011 | Jung et al. |
| 7,976,480 B2 | 7/2011 | Grajales et al. |
| 7,983,933 B2 | 7/2011 | Karkanias et al. |
| 8,047,998 B2 | 11/2011 | Kolluri et al. |
| 8,082,160 B2 | 12/2011 | Collins, Jr. et al. |
| 8,137,270 B2 | 3/2012 | Keenan et al. |
| 8,167,800 B2 | 5/2012 | Ouchi et al. |
| 2001/0004234 A1 | 6/2001 | Petelenz et al. |
| 2001/0007923 A1 | 7/2001 | Yamamoto |
| 2001/0013826 A1 | 8/2001 | Ahmed et al. |
| 2002/0013517 A1 | 1/2002 | West et al. |
| 2002/0032386 A1 | 3/2002 | Sackner et al. |
| 2002/0072859 A1 | 6/2002 | Kajimoto et al. |
| 2002/0151805 A1 | 10/2002 | Sugo et al. |
| 2002/0156354 A1 | 10/2002 | Larson |
| 2002/0170193 A1 | 11/2002 | Townsend et al. |
| 2002/0183627 A1 | 12/2002 | Nishii et al. |
| 2002/0193671 A1 | 12/2002 | Ciurczak et al. |
| 2002/0193692 A1 | 12/2002 | Inukai et al. |
| 2002/0198679 A1 | 12/2002 | Victor et al. |
| 2003/0004420 A1 | 1/2003 | Narimatsu |
| 2003/0130590 A1 | 7/2003 | Bui et al. |
| 2003/0135099 A1 | 7/2003 | Al-Ali |
| 2003/0153836 A1 | 8/2003 | Gagnadre et al. |
| 2003/0158699 A1 | 8/2003 | Townsend et al. |
| 2003/0167012 A1 | 9/2003 | Friedman et al. |
| 2003/0171662 A1 | 9/2003 | O'Connor et al. |
| 2003/0181815 A1 | 9/2003 | Ebner et al. |
| 2003/0208335 A1 | 11/2003 | Unuma et al. |
| 2004/0019288 A1 | 1/2004 | Kinast |
| 2004/0030261 A1 | 2/2004 | Rantala |
| 2004/0034293 A1 | 2/2004 | Kimball |
| 2004/0034294 A1 | 2/2004 | Kimball et al. |
| 2004/0054821 A1 | 3/2004 | Warren et al. |
| 2004/0073128 A1 | 4/2004 | Hatlestad et al. |
| 2004/0077934 A1 | 4/2004 | Massad |
| 2004/0122315 A1 | 6/2004 | Krill |
| 2004/0133079 A1 | 7/2004 | Mazar et al. |
| 2004/0162466 A1 | 8/2004 | Quy |
| 2004/0162493 A1 | 8/2004 | Mills |
| 2004/0225207 A1 | 11/2004 | Bae et al. |
| 2004/0267099 A1 | 12/2004 | McMahon et al. |
| 2005/0027205 A1 | 2/2005 | Tarassenko et al. |
| 2005/0043598 A1 | 2/2005 | Goode, Jr. et al. |
| 2005/0059870 A1 | 3/2005 | Aceti |
| 2005/0070773 A1 | 3/2005 | Chin et al. |
| 2005/0075550 A1* | 4/2005 | Lindekugel .................. 600/344 |
| 2005/0113107 A1 | 5/2005 | Meunier |
| 2005/0113703 A1 | 5/2005 | Farringdon et al. |
| 2005/0119586 A1 | 6/2005 | Coyle et al. |
| 2005/0119833 A1 | 6/2005 | Nanikashvili |
| 2005/0124866 A1 | 6/2005 | Elaz et al. |
| 2005/0124903 A1 | 6/2005 | Roteliuk et al. |
| 2005/0149350 A1 | 7/2005 | Kerr et al. |
| 2005/0171444 A1 | 8/2005 | Ono et al. |
| 2005/0187796 A1 | 8/2005 | Rosenfeld et al. |
| 2005/0206518 A1 | 9/2005 | Welch et al. |
| 2005/0209511 A1 | 9/2005 | Heruth et al. |
| 2005/0228296 A1 | 10/2005 | Banet |
| 2005/0228298 A1 | 10/2005 | Banet et al. |
| 2005/0228301 A1 | 10/2005 | Banet et al. |
| 2005/0234317 A1 | 10/2005 | Kiani |
| 2005/0240087 A1 | 10/2005 | Keenan et al. |
| 2005/0261565 A1 | 11/2005 | Lane et al. |
| 2005/0261593 A1 | 11/2005 | Zhang et al. |
| 2005/0265267 A1 | 12/2005 | Hwang |
| 2005/0283088 A1 | 12/2005 | Bernstein |
| 2006/0036141 A1 | 2/2006 | Kamath et al. |
| 2006/0047215 A1 | 3/2006 | Newman et al. |
| 2006/0074321 A1 | 4/2006 | Kouchi et al. |
| 2006/0074322 A1 | 4/2006 | Nitzan |
| 2006/0128263 A1 | 6/2006 | Baird |
| 2006/0142648 A1 | 6/2006 | Banet et al. |
| 2006/0155589 A1 | 7/2006 | Lane et al. |
| 2006/0178591 A1 | 8/2006 | Hempfling |
| 2006/0200029 A1 | 9/2006 | Evans et al. |
| 2006/0252999 A1 | 11/2006 | Devaul et al. |
| 2006/0265246 A1 | 11/2006 | Hoag |
| 2006/0270949 A1 | 11/2006 | Mathie et al. |
| 2006/0271404 A1 | 11/2006 | Brown |
| 2006/0281979 A1 | 12/2006 | Kim et al. |
| 2007/0010719 A1 | 1/2007 | Huster et al. |
| 2007/0055163 A1 | 3/2007 | Asada et al. |
| 2007/0066910 A1 | 3/2007 | Inukai et al. |
| 2007/0071643 A1 | 3/2007 | Hall et al. |
| 2007/0094045 A1 | 4/2007 | Cobbs et al. |
| 2007/0118056 A1 | 5/2007 | Wang et al. |
| 2007/0129769 A1 | 6/2007 | Bourget et al. |
| 2007/0142715 A1 | 6/2007 | Banet et al. |
| 2007/0156456 A1 | 7/2007 | McGillin et al. |
| 2007/0161912 A1 | 7/2007 | Zhang et al. |
| 2007/0185393 A1 | 8/2007 | Zhou et al. |
| 2007/0188323 A1 | 8/2007 | Sinclair et al. |
| 2007/0193834 A1 | 8/2007 | Pai et al. |
| 2007/0208233 A1 | 9/2007 | Kovacs |
| 2007/0232867 A1 | 10/2007 | Hansmann |
| 2007/0237719 A1 | 10/2007 | Jones et al. |
| 2007/0244376 A1 | 10/2007 | Wang |
| 2007/0250261 A1 | 10/2007 | Soehren |
| 2007/0252853 A1 | 11/2007 | Park et al. |
| 2007/0255116 A1 | 11/2007 | Mehta et al. |
| 2007/0260487 A1 | 11/2007 | Bartfeld et al. |
| 2007/0265533 A1 | 11/2007 | Tran |
| 2007/0265880 A1 | 11/2007 | Bartfeld et al. |
| 2007/0270671 A1 | 11/2007 | Gal |
| 2007/0276261 A1 | 11/2007 | Banet et al. |
| 2007/0282208 A1 | 12/2007 | Jacobs et al. |
| 2007/0287386 A1 | 12/2007 | Agrawal et al. |
| 2007/0293770 A1 | 12/2007 | Bour et al. |
| 2007/0293781 A1 | 12/2007 | Sims et al. |
| 2008/0004500 A1 | 1/2008 | Cazares et al. |
| 2008/0004507 A1 | 1/2008 | Williams, Jr. et al. |
| 2008/0004904 A1 | 1/2008 | Tran |
| 2008/0027341 A1 | 1/2008 | Sackner et al. |
| 2008/0033255 A1 | 2/2008 | Essenpreis et al. |

(56) References Cited

U.S. PATENT DOCUMENTS

| | | |
|---|---|---|
| 2008/0039731 A1 | 2/2008 | McCombie et al. |
| 2008/0077027 A1 | 3/2008 | Allgeyer |
| 2008/0082001 A1 | 4/2008 | Hatlestad et al. |
| 2008/0101160 A1 | 5/2008 | Besson |
| 2008/0103405 A1 | 5/2008 | Banet et al. |
| 2008/0114220 A1 | 5/2008 | Banet et al. |
| 2008/0132106 A1 | 6/2008 | Burnes et al. |
| 2008/0139955 A1 | 6/2008 | Hansmann et al. |
| 2008/0146887 A1 | 6/2008 | Rao et al. |
| 2008/0146892 A1 | 6/2008 | Leboeuf et al. |
| 2008/0161707 A1 | 7/2008 | Farringdon et al. |
| 2008/0162496 A1 | 7/2008 | Postrel |
| 2008/0167535 A1 | 7/2008 | Stivoric et al. |
| 2008/0171927 A1 | 7/2008 | Yang et al. |
| 2008/0194918 A1 | 8/2008 | Kulik et al. |
| 2008/0195735 A1 | 8/2008 | Hodges et al. |
| 2008/0204254 A1 | 8/2008 | Kazuno |
| 2008/0208013 A1 | 8/2008 | Zhang et al. |
| 2008/0208273 A1 | 8/2008 | Owen et al. |
| 2008/0214963 A1 | 9/2008 | Guillemaud et al. |
| 2008/0221399 A1 | 9/2008 | Zhou et al. |
| 2008/0221404 A1 | 9/2008 | Tso |
| 2008/0262362 A1 | 10/2008 | Kolluri et al. |
| 2008/0275349 A1 | 11/2008 | Halperin et al. |
| 2008/0281168 A1 | 11/2008 | Gibson et al. |
| 2008/0281310 A1 | 11/2008 | Dunning et al. |
| 2008/0287751 A1 | 11/2008 | Stivoric et al. |
| 2008/0294019 A1 | 11/2008 | Tran |
| 2008/0319282 A1 | 12/2008 | Tran |
| 2008/0319327 A1 | 12/2008 | Banet et al. |
| 2009/0018408 A1 | 1/2009 | Ouchi et al. |
| 2009/0018409 A1 | 1/2009 | Banet et al. |
| 2009/0018453 A1 | 1/2009 | Banet et al. |
| 2009/0040041 A1 | 2/2009 | Janetis et al. |
| 2009/0054752 A1 | 2/2009 | Jonnalagadda et al. |
| 2009/0069642 A1 | 3/2009 | Gao et al. |
| 2009/0076363 A1 | 3/2009 | Bly et al. |
| 2009/0076397 A1 | 3/2009 | Libbus et al. |
| 2009/0076398 A1 | 3/2009 | Li et al. |
| 2009/0076405 A1 | 3/2009 | Amurthur et al. |
| 2009/0082681 A1 | 3/2009 | Yokoyama et al. |
| 2009/0112072 A1 | 4/2009 | Banet et al. |
| 2009/0112281 A1 | 4/2009 | Miyazawa et al. |
| 2009/0112630 A1 | 4/2009 | Collins, Jr. et al. |
| 2009/0118590 A1 | 5/2009 | Teller et al. |
| 2009/0118626 A1 | 5/2009 | Moon et al. |
| 2009/0131759 A1 | 5/2009 | Sims et al. |
| 2009/0187085 A1 | 7/2009 | Pav |
| 2009/0192366 A1 | 7/2009 | Mensinger et al. |
| 2009/0198139 A1 | 8/2009 | Lewicke et al. |
| 2009/0221937 A1 | 9/2009 | Smith et al. |
| 2009/0222119 A1 | 9/2009 | Plahey et al. |
| 2009/0227877 A1 | 9/2009 | Tran |
| 2009/0233770 A1 | 9/2009 | Vincent et al. |
| 2009/0259113 A1 | 10/2009 | Liu et al. |
| 2009/0262074 A1 | 10/2009 | Nasiri et al. |
| 2009/0264712 A1 | 10/2009 | Baldus et al. |
| 2009/0287067 A1 | 11/2009 | Dorogusker et al. |
| 2009/0295541 A1 | 12/2009 | Roof |
| 2009/0306485 A1 | 12/2009 | Bell |
| 2009/0306487 A1 | 12/2009 | Crowe et al. |
| 2009/0306524 A1 | 12/2009 | Muhlsteff et al. |
| 2009/0312973 A1 | 12/2009 | Hatlestad et al. |
| 2009/0318779 A1 | 12/2009 | Tran |
| 2009/0322513 A1 | 12/2009 | Hwang et al. |
| 2009/0326349 A1 | 12/2009 | McGonigle et al. |
| 2010/0010380 A1 | 1/2010 | Panken et al. |
| 2010/0030034 A1 | 2/2010 | Schulhauser et al. |
| 2010/0030085 A1 | 2/2010 | Rojas Ojeda et al. |
| 2010/0056881 A1 | 3/2010 | Libbus et al. |
| 2010/0056886 A1 | 3/2010 | Hurtubise et al. |
| 2010/0113948 A1 | 5/2010 | Yang et al. |
| 2010/0125188 A1 | 5/2010 | Schilling et al. |
| 2010/0130811 A1 | 5/2010 | Leuthardt et al. |
| 2010/0160793 A1 | 6/2010 | Lee et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168589 A1 | 7/2010 | Banet et al. |
| 2010/0210930 A1 | 8/2010 | Saylor |
| 2010/0217099 A1 | 8/2010 | Leboeuf et al. |
| 2010/0222649 A1 | 9/2010 | Schoenberg |
| 2010/0234693 A1 | 9/2010 | Srinivasan et al. |
| 2010/0234786 A1 | 9/2010 | Fulkerson et al. |
| 2010/0241011 A1 | 9/2010 | McCombie et al. |
| 2010/0280440 A1 | 11/2010 | Skelton et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0312115 A1 | 12/2010 | Dentinger |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2010/0331640 A1 | 12/2010 | Medina |
| 2011/0066006 A1 | 3/2011 | Banet et al. |
| 2011/0066007 A1 | 3/2011 | Banet et al. |
| 2011/0066008 A1 | 3/2011 | Banet et al. |
| 2011/0066009 A1 | 3/2011 | Moon et al. |
| 2011/0066010 A1 | 3/2011 | Moon et al. |
| 2011/0066037 A1 | 3/2011 | Banet et al. |
| 2011/0066038 A1 | 3/2011 | Banet et al. |
| 2011/0066039 A1 | 3/2011 | Banet et al. |
| 2011/0066043 A1 | 3/2011 | Banet et al. |
| 2011/0066044 A1 | 3/2011 | Moon et al. |
| 2011/0066045 A1 | 3/2011 | Moon et al. |
| 2011/0066050 A1 | 3/2011 | Moon et al. |
| 2011/0066051 A1 | 3/2011 | Moon et al. |
| 2011/0066062 A1 | 3/2011 | Banet et al. |
| 2011/0070829 A1 | 3/2011 | Griffin et al. |
| 2011/0076942 A1 | 3/2011 | Taveau et al. |
| 2011/0093281 A1 | 4/2011 | Plummer et al. |
| 2011/0105862 A1 | 5/2011 | Gies et al. |
| 2011/0144456 A1 | 6/2011 | Muhlsteff et al. |
| 2011/0152632 A1 | 6/2011 | Le Neel et al. |
| 2011/0178375 A1 | 7/2011 | Forster |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257554 A1 | 10/2011 | Banet et al. |
| 2011/0257555 A1 | 10/2011 | Banet et al. |
| 2011/0275907 A1 | 11/2011 | Inciardi et al. |
| 2012/0065525 A1 | 3/2012 | Douniama et al. |
| 2012/0123232 A1 | 5/2012 | Najarian et al. |

FOREIGN PATENT DOCUMENTS

| | | |
|---|---|---|
| GB | 2329250 A | 3/1999 |
| WO | 1999032030 A1 | 7/1999 |
| WO | 2006005169 A1 | 1/2006 |
| WO | 2007024777 A2 | 3/2007 |
| WO | 2007143535 A2 | 12/2007 |

(56) References Cited

FOREIGN PATENT DOCUMENTS

| WO | 2008037820 A1 | 4/2008 |
|---|---|---|
| WO | 2008110788 A1 | 9/2008 |
| WO | 2009009761 A1 | 1/2009 |
| WO | 2010135516 A2 | 11/2010 |
| WO | 2010135518 A1 | 11/2010 |
| WO | 2010148205 A1 | 12/2010 |
| WO | 2011032132 A2 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |

OTHER PUBLICATIONS

Non-Final Office Action issued by the US Patent and Trademark Office dated Sep. 14, 2012 in U.S. Appl. No. 12/650,374.
Drinnan et al., Relation between heart rate and pulse transit time during paced respiration. Physiol. Meas. Aug. 2001;22(3):425-432.
Flash et al., The Coordination of Arm Movements: An Experimentally Confirmed Mathematical Model. J Neurosci. Jul. 1985;5(7):1688-1703.
Ma and Zhang, A Correlation Study on the Variabilities in Pulse Transit Time, Blood Pressure, and Heart Rate Recorded Simultaneously from Healthy Subjects. Conf Proc IEEE Eng Med Biol Soc. 2005;1:996-999.
Non-Final Office Action issued by the US Patent and Trademark Office dated Sep. 17, 2012 in U.S. Appl. No. 12/469,192.
Gallagher, Comparison of Radial and Femoral Arterial Blood Pressure in Children after Cardiopulmonary Bypass. J Clin Monit. Jul. 1985;1(3):168-171.
Park et al., Direct Blood Pressure Measurements in Brachial and Femoral Arteries in Children. Circulation Feb. 1970;41(2)231-237.
Talkowski, Quantifying Physical Activity in Community Dwelling Older Adults Using Accelerometry. University of Pittsburgh (Dissertation) 2008:1-91.
Non-Final Office Action issued by the US Patent and Trademark Office dated Sep. 26, 2012 in U.S. Appl. No. 12/560,104.
Packet Definition. The Linux Information Project Jan. 8, 2006 http://www.linfo.org/packet.html.
RS-232. Wikipedia Dec. 5, 2008 http:I/web.archive.org/web/20081205160754/http:/!en.wikipedia.org/wiki/RS-232.
Non-Final Office Action issued by the US Patent and Trademark Office dated Oct. 9, 2012 in U.S. Appl. No. 12/762,726.
Final Office Action issued by the US Patent and Trademark Office dated Oct. 22, 2012 in U.S. Appl. No. 12/762,822.
Final Office Action issued by the US Patent and Trademark Office dated Oct. 25, 2012 in U.S. Appl. No. 12/599,426.
Alves et al., CAN Protocol: A Laboratory Prototype for Fieldbus Applications. XIX IMEKO World Congress Fundamental and Applied Metrology Sep. 6-11, 2009, Lisbon, Portugal. 4 pages :454-457 ISBN 978-963-88410-0-1.
Benefits of Digital Sensors. Gems Sensors. Feb. 14, 2008. http://web.archive.org/web/20080214122230/http://www.sensorland.com/HowPage054.html.
Final Office Action issued by the US Patent and Trademark Office dated Oct. 25, 2012 in U.S. Appl. No. 12/762,790.
Non-Final Office Action issued by the US Patent and Trademark Office dated Oct. 30, 2012 in U.S. Appl. No. 12/559,386.
Non-Final Office Action issued by the US Patent and Trademark Office dated Nov. 6, 2012 in U.S. Appl. No. 12/559,379.
Non-Final Office Action issued by the US Patent and Trademark Office dated Nov. 6, 2012 in U.S. Appl. No. 12/650,370.
Poon and Zhang, Cuff-Less and Noninvasive Measurements of Arterial Blood Pressure by Pulse Transit Time. Conf Proc IEEE Eng Med Biol Soc. 2005;6:5877-5880.
Non-Final Office Action issued by the US Patent and Trademark Office dated Nov. 7, 2012 in U.S. Appl. No. 12/559,392.
Non-Final Office Action issued by the US Patent and Trademark Office dated Jul. 18, 2012 in U.S. Appl. No. 12/650,389.
Chan et al., Noninvasive and Cuffless Measurements of Blood Pressure for Telemedicine. Proceedings of the 23rd Annual International Conference of the IEEE Engineering in Medicine and Biology Society 2001:3 pages.
Fung, Advisory System for Administration of Phenylephrine Following Spinal Anesthesia for Cesarean Section. Master's Thesis. University of British Columbia 2002: 119 pages.
Liu et al., The Changes in Pulse Transit Time at Specific Cuff Pressures during Inflation and Deflation. Proceedings of the 28th IEEE EMBS Annual International Conference New York City, USA, Aug. 30-Sep. 3, 2006:6404-6405.
Nitzan et al., Effects of External Pressure on Arteries Distal to the Cuff During Sphygmomanometry. IEEE Transactions on Biomedical Engineering, Jun. 2005;52(6):1120-1127.
USB 2.0 Specification Engineering Change Notice. Oct. 20, 2000.
Yan and Zhang, A Novel Calibration Method for Noninvasive Blood Pressure Measurement Using Pulse Transit Time. Proceedings of the 4th IEEE-EMBS International Summer School and Symposium on Medical Devices and Biosensors St Catharine's College,Cambridge, UK, Aug. 19-22, 2007.
Zislin et al., Ways of Improving the Accuracy of Arterial Pressure Oscillometry. Biomedical Engineering 2005;39(4):174-178.
International Search Report and Written Opinion dated May 29, 2012 issued in PCT/US2012/025648.
Non-Final Office Action issued by the US Patent and Trademark Office dated Aug. 3, 2012 in U.S. Appl. No. 12/762,925.
Non-Final Office Action issued by the US Patent and Trademark Office dated Aug. 3, 2012 in U.S. Appl. No. 12/762,963.
Non-Final Office Action issued by the US Patent and Trademark Office dated Aug. 20, 2012 in U.S. Appl. No. 12/762,777.
Non-Final Office Action issued by the US Patent and Trademark Office dated Aug. 21, 2012 in U.S. Appl. No. 12/469,107.
Non-Final Office Action issued by the US Patent and Trademark Office dated Aug. 24, 2012 in U.S. Appl. No. 12/762,936.
International Search Report and Written Opinion dated Jul. 22, 2011 issued in PCT/US2011/027843.
International Search Report and Written Opinion dated Jul. 20, 2011 issued in PCT/US2011/033100.
Non-Final Office Action issued by the US Patent and Trademark Office dated May 26, 2011 in U.S. Appl. No. 12/469,151.
Response to Non-Final Office Action dated Nov. 25, 2011 in U.S. Appl. No. 12/469,151.
Notice of Allowance issued by the US Patent and Trademark Office dated Feb. 1, 2012 in U.S. Appl. No. 12/469,151.
Non-Final Office Action issued by the US Patent and Trademark Office dated Aug. 4, 2011 in U.S. Appl. No. 12/469,182.
Response to Non-Final Office Action dated Nov. 25, 2011 in U.S. Appl. No. 12/469,182.
Notice of Allowance issued by the US Patent and Trademark Office dated Dec. 28, 2011 in U.S. Appl. No. 12/469,182.
International Search Report and Written Opinion dated Oct. 15, 2010 issued in PCT/US2010/035550.
Non-Final Office Action issued by the US Patent and Trademark Office dated Apr. 12, 2012 in U.S. Appl. No. 12/559,429.
Non-Final Office Action issued by the US Patent and Trademark Office dated Apr. 12, 2012 in U.S. Appl. No. 12/559,430.
Non-Final Office Action issued by the US Patent and Trademark Office dated Apr. 24, 2012 in U.S. Appl. No. 12/559,435.
Non-Final Office Action issued by the US Patent and Trademark Office dated Apr. 25, 2012 in U.S. Appl. No. 12/762,733.
Non-Final Office Action issued by the US Patent and Trademark Office dated Apr. 27, 2012 in U.S. Appl. No. 12/762,822.
Non-Final Office Action issued by the US Patent and Trademark Office dated Mar. 27, 2012 in U.S. Appl. No. 12/559,422.
Mathie, Monitoring and Interpreting Human Movement Patterns using a Triaxial Accelerometer. Faculty of Engineering. The University of New South Wales. PhD Dissertation. Aug. 2003: part1 pp. 1-256.
Mathie, Monitoring and Interpreting Human Movement Patterns using a Triaxial Accelerometer. Faculty of Engineering. The University of New South Wales. PhD Dissertation. Aug. 2003: part2 pp. 256-512.

(56) References Cited

OTHER PUBLICATIONS

International Search Report and Written Opinion dated Apr. 27, 2012 as reported in PCT/US2011/067441.
Non-Final Office Action issued by the US Patent and Trademark Office dated May 7, 2012 in U.S. Appl. No. 12/469,115.
Non-Final Office Action issued by the US Patent and Trademark Office dated May 9, 2012 in U.S. Appl. No. 12/762,836.
Non-Final Office Action issued by the US Patent and Trademark Office dated May 10, 2012 in U.S. Appl. No. 12/559,419.
Jackson, Digital Filter Design and Synthesis Using High-Level Modeling Tools. Virginia Polytechnic Institute and State University Thesis. Dec. 1999.
Kim et al., Two Algorithms for Detecting Respiratory Rate from ECG Signal. IFMBE Proceedings 2007;14(6) JC27:4069-4071.
O'Haver, Peak Finding and Measurement, Version 1.6 Oct. 26, 2006. http://web.archive.org/web/20090205162604/http://terpconnect.umd.edu/-toh/spectrum/PeakFindingandMeasurement.htm.
Reinvuo et al., Measurement of Respiratory Rate with High-Resolution Accelerometer and EMFit Pressure Sensor. Proceedings of the 2006 IEEE Sensors Applications Symposium Feb. 7-9, 2006:192-195.
Non-Final Office Action issued by the US Patent and Trademark Office dated May 11, 2012 in U.S. Appl. No. 12/762,846.
Non-Final Office Action issued by the US Patent and Trademark Office dated May 11, 2012 in U.S. Appl. No. 12/762,874.
Non-Final Office Action issued by the US Patent and Trademark Office dated Jun. 11, 2012 in U.S. Appl. No. 12/469,222.
Non-Final Office Action issued by the US Patent and Trademark Office dated Jun. 8, 2012 in U.S. Appl. No. 12/650,383.
Non-Final Office Action issued by the US Patent and Trademark Office dated Jun. 8, 2012 in U.S. Appl. No. 12/650,392.
Non-Final Office Action issued by the US Patent and Trademark Office dated Jun. 20, 2012 in U.S. Appl. No. 12/762,751.
International Search Report and Written Opinion dated Jun. 29, 2012 issued in PCT/US2012/025640.
Non-Final Office Action issued by the US Patent and Trademark Office dated Jul. 5, 2012 in U.S. Appl. No. 12/560,138.
"Signal Strength." Oct. 6, 2008. http://web.archive.org/web/20081006200523/http://!en.wikipedia.org/wiki/Signal_strength.
Non-Final Office Action issued by the US Patent and Trademark Office dated May 24, 2012 in U.S. Appl. No. 12/560,111.
Restriction Requirement issued by the US Patent and Trademark Office dated Apr. 24, 2012 in U.S. Appl. No. 12/469,107.
Response to Restriction Requirement dated Jun. 14, 2012 in U.S. Appl. No. 12/469,107.
Final Office Action issued by the United States Patent and Trademark Office in U.S. Appl. No. 12/469,236 dated Jul. 8, 2013.
Non-Final Office Action issued by the United States Patent and Trademark Office in U.S. Appl. No. 12/560,111 dated Jul. 8, 2013.
Scanaill et al., A Review of Approaches to Mobility Telemonitoring of the Elderly in Their Living Environment. Annals of Biomed Engineer. Apr. 2006;34(4):547-563.
Notice of Allowance issued by the United States Patent and Trademark Office in U.S. Appl. No. 12/762,733 dated Jul. 24, 2013.
Final Office Action issued by the United States Patent and Trademark Office in application No. 12/762,944 dated Aug. 2, 2013.
Response to Office Action issued by the United States Patent and Trademark Office in application No. 12/559,039 dated Aug. 9, 2013.
Sifil et al., Evaluation of the Harmonized Alert Sensing Technology Device for Hemodynamic Monitoring in Chronic Hemodialysis Patients. ASAIO J. Nov.-Dec. 2003;49(6):667-672.
Weinhold et al., Buprenorphine alone and in combination with naloxone in non-dependent humans. Drug Alcohol Depend. Aug. 1992;30(3):263-274.
Final Office Action issued by the United States Patent and Trademark Office in application No. 12/762,726 dated Aug. 15, 2013.
Extended European Search Report and Written Opinion issued in application No. EP 10817733 dated Aug. 29, 2013.
Extended European Search Report and Written Opinion issued in application No. EP 08770884 dated Sep. 17, 2013.

Allen et al., Classification of a known sequence of motions and postures from accelerometry data using adapted Gaussian mixture models. Physiol. Meas. 2006;27:935-951.
Asada et al., Active Noise Cancellation Using MEMS Accelerometers for Motion-Tolerant Wearable Bio-Sensors. Proceedings of the 26th Annual International Conference of the IEEE EMBS. San Francisco, CA, USA. Sep. 1-5, 2004:2157-2160.
Bowers et al., Respiratory Rate Derived from Principal Component Analysis of Single Lead Electrocardiogram. Computers in Cardiology Conference Proceedings Sep. 2008;35:437-440.
Bussmann et al., Measuring daily behavior using ambulatory accelerometry: The Activity Monitor. Behav Res Methods Instrum Comput. Aug. 2001;33(3):349-356.
Cretikos et al., The Objective Medical Emergency Team Activation Criteria: a case-control study. Resuscitation Apr. 2007;73(1):62-72.
Espina et al., Wireless Body Sensor Network for Continuous Cuff-less Blood Pressure Monitoring. Proceedings of the 3rd IEEE-EMBS. International Summer School and Symposium on Medical Devices and Biosensors. MIT, Boston, USA, Sep. 4-6, 2006:11-15.
Fieselmann et al., Respiratory rate predicts cardiopulmonary arrest for internal medicine patients. J Gen Intern Med Jul. 1993;8(7):354-360.
Goldhill et al., A physiologically-based early warning score for ward patients: the association between score and outcome. Anaesthesia Jun. 2005;60(6):547-553.
Hung et al., Estimation of Respiratory Waveform Using an Accelerometer. 5th IEEE International Symposium on Biomedical Imaging: From Nano to Macro, May 14-17, 2008:1493-1496.
Jin, A Respiration Monitoring System Based on a Tri-Axial Accelerometer and an Air-Coupled Microphone. Technische Universiteit Eindhoven, University of Technology. Master's Graduation Paper, Electrical Engineering Aug. 25, 2009.
Karantonis et al., Implementation of a Real-Time Human Movement Classifier Using a Triaxial Accelerometer for Ambulatory Monitoring. IEEE Transactions on Information Technology in Biomedicine. Jan. 2006;10(1):156-167.
Khambete et al., Movement artefact rejection in impedance pneumography using six strategically placed electrodes. Physiol. Meas. 2000;21:79-88.
Khan et al., Accelerometer Signal-based Human Activity Recognition Using Augmented Autoregressive Model Coefficients and Artificial w Neural Nets. 30th Annual International Conference of the IEEE Engineering in Medicine and Biology Society. Aug. 20-24, 2008:5172-5175.
Mason, Signal Processing Methods for Non-Invasive Respiration Monitoring. Department of Engineering Science, University of Oxford 2002.
Mathie et al., Classification of basic daily movements using a triaxial accelerometer. Med Biol Eng Comput. Sep. 2004;42(5):679-687.
Otto et al., System Architecture of a Wireless Body Area Sensor Network for Ubiquitous Health Monitoring. Journal of Mobile Multimedia Jan. 10, 2006;1(4):307-326.
Park et al., An improved algorithm for respiration signal extraction from electrocardiogram measured by conductive textile electrodes using instantaneous frequency estimation. Med Bio Eng Comput 2008;46:147-158.
PDF-Pro for iPhone & iPod touch User Manual. ePapyrus Jul. 2009;1:1-25 http://epapyrus.com/en/files/PDFPro%.
Seo et al., Performance Improvement of Pulse Oximetry-Based Respiration Detection by Selective Mode Bandpass Filtering. Ergonomics and Health Aspects of Work with Computers Lecture Notes in Computer Science, 2007;4566:300-308.
Soh et al., An investigation of respiration while wearing back belts. Applied Ergonomics 1997; 28(3):189-192.
Subbe et al., Effect of introducing the Modified Early Warning score on clinical outcomes, cardiopulmonary arrests and intensive care utilization in acute medical admissions. Anaesthesia Aug. 2003;58(8):797-802.
Vuorela et al., Two portable long-term measurement devices for ECG and bioimpedance. Second International Conference on Pervasive Computing Technologies for Healthcare.. Jan. 30-Feb. 1, 2008: 169-172.

(56) References Cited

OTHER PUBLICATIONS

Wolf et al., Development of a Fall Detector and Classifier based on a Triaxial Accelerometer Demo Board. 2007:210-213.
Non-Final Office Action issued by the US Patent and Trademark Office dated Apr. 30, 2012 in U.S. Appl. No. 12/762,790.
Non-Final Office Action issued by the US Patent and Trademark Office dated Mar. 30, 2012 in U.S. Appl. No. 12/469,236.
Non-Final Office Action issued by the US Patent and Trademark Office dated Apr. 3, 2012 in U.S. Appl. No. 12/469,094.
Restriction Requirement issued by the US Patent and Trademark Office dated Feb. 2, 2012 in U.S. Appl. No. 12/469,222.
Non-Final Office Action issued by the US Patent and Trademark Office dated Mar. 27, 2012 in U.S. Appl. No. 12/559,426.
Non-Final Office Action issued by the US Patent and Trademark Office dated Apr. 3, 2012 in U.S. Appl. No. 12/559,039.
Non-Final Office Action issued by the US Patent and Trademark Office dated Dec. 29, 2011 in U.S. Appl. No. 12/559,080.
Response to Non-Final Office Action dated Mar. 19, 2012 in U.S. Appl. No. 12/559,080.
Notice of Allowance issued by the US Patent and Trademark Office dated Apr. 2, 2012 in U.S. Appl. No. 12/559,080.
Non-Final Office Action issued by the US Patent and Trademark Office dated Dec. 15, 2011 in U.S. Appl. No. 12/560,077.
Non-Final Office Action issued by the US Patent and Trademark Office dated Mar. 8, 2012 in U.S. Appl. No. 12/560,093.
Restriction Requirement issued by the US Patent and Trademark Office dated Dec. 14, 2012 in U.S. Appl. No. 12/560,093.
Response to Restriction Requirement dated Feb. 15, 2012 in U.S. Appl. No. 12/560,093.
Non-Final Office Action issued by the US Patent and Trademark Office dated Mar. 1, 2012 in U.S. Appl. No. 12/560,104.
Restriction Requirement issued by the US Patent and Trademark Office dated Jan. 19, 2012 in U.S. Appl. No. 12/469,115.
Response to Restriction Requirement dated Feb. 15, 2012 in U.S. Appl. No. 12/469,115.
Restriction Requirement issued by the US Patent and Trademark Office dated Nov. 14, 2011 in U.S. Appl. No. 12/469,127.
Response to Restriction Requirement dated Feb. 15, 2012 in U.S. Appl. No. 12/469,127.
Non-Final Office Action issued by the US Patent and Trademark Office dated Mar. 9, 2012 in U.S. Appl. No. 12/469,127.
Non-Final Office Action issued by the US Patent and Trademark Office dated Apr. 3, 2012 in U.S. Appl. No. 12/469,137.
International Preliminary Report on Patentability dated Dec. 1, 2011 issued in PCT/US2010/035554.
International Search Report and Written Opinion dated Sep. 23, 2010 issued in PCT/US2010/035554.
International Preliminary Report on Patentability dated Jan. 5, 2012 issued in PCT/US2010/039000.
International Search Report and Written Opinion dated Sep. 7, 2010 issued in PCT/US2010/039000.
International Search Report and Written Opinion dated Nov. 3, 2010 issued in PCT/US2010/048729.
International Search Report and Written Opinion dated Nov. 5, 2010 issued in PCT/US2010/048866.
International Search Report and Written Opinion dated Mar. 3, 2011 issued in PCT/US2010/062564.
Non-Final Office Action issued by the US Patent and Trademark Office dated Aug. 30, 2012 in U.S. Appl. No. 12/469,202.
Non-Final Office Action issued by the US Patent and Trademark Office dated Sep. 17, 2012 in U.S. Appl. No. 12/650,354.
Non-Final Office Action issued by the US Patent and Trademark Office dated Sep. 21, 2012 in U.S. Appl. No. 12/469,115.
Response to Non-Final Office Action issued in U.S. Appl. No. 12/469,236 dated Sep. 27, 2012.
Response to Non-Final Office Action issued in U.S. Appl. No. 12/487,283 dated Sep. 27, 2012.
Non-Final Office Action issued by the US Patent and Trademark Office dated Sep. 28, 2012 in U.S. Appl. No. 12/560,087.
Response to Non-Final Office Action issued in U.S. Appl. No. 12/762,836 dated Oct. 9, 2012.
Response to Non-Final Office Action issued in U.S. Appl. No. 12/559,429 dated Oct. 12, 2012.
Response to Non-Final Office Action issued in U.S. Appl. No. 12/559,430 dated Oct. 12, 2012.
Response to Non-Final Office Action issued in U.S. Appl. No. 12/559,435 dated Oct. 23, 2012.
Final Office Action issued by the US Patent and Trademark Office dated Oct. 24, 2012 in U.S. Appl. No. 12/599,429.
Final Office Action issued by the US Patent and Trademark Office dated Oct. 24, 2012 in U.S. Appl. No. 12/599,430.
Non-Final Office Action issued by the US Patent and Trademark Office dated Oct. 23, 2012 in U.S. Appl. No. 12/762,944.
Response to Non-Final Office Action issued in U.S. Appl. No. 12/762,733 dated Oct. 25, 2012.
Final Office Action issued by the US Patent and Trademark Office dated Oct. 26, 2012 in U.S. Appl. No. 12/762,836.
Non-Final Office Action issued by the US Patent and Trademark Office dated Oct. 24, 2012 in U.S. Appl. No. 12/559,403.
Non Final Office Action issued by the United States Patent and Trademark Office in U.S. Appl. No. 12/559,413 dated Nov. 9, 2012.
Response to Office Action issued in U.S. Appl. No. 12/762,846 dated Nov. 13, 2012.
Response to Office Action issued in U.S. Appl. No. 12/762,874 dated Nov. 13, 2012.
Response to Office Action issued in U.S. Appl. No. 12/560,111 dated Nov. 26, 2012.
Response to Office Action issued in U.S. Appl. No. 11/930,881 dated Nov. 26, 2012.
Final Rejection issued by the United States Patent and Trademark Office in U.S. Appl. No. 12/559,419 dated Nov. 16, 2012.
Non Final Office Action issued by the United States Patent and Trademark Office in U.S. Appl. No. 12/559,408 dated Nov. 23, 2012.
Response to Office Action issued in U.S. Appl. No. 12/138,199 dated Nov. 29, 2012.
Response to Office Action issued in U.S. Appl. No. 12/650,383 dated Dec. 7, 2012.
Response to Office Action issued in U.S. Appl. No. 12/650,392 dated Dec. 7, 2012.
Final Rejection issued by the United States Patent and Trademark Office in U.S. Appl. No. 12/559,435 dated Dec. 12, 2012.
Final Rejection issued by the United States Patent and Trademark Office in U.S. Appl. No. 12/560,111 dated Dec. 12, 2012.
Clifford et al., Measuring Tilt with Low-g Accelerometers. Freescale Semiconductor, Inc., 2005:8 pages.
McKneely et al., Plug-and-Play and Network-Capable Medical Instrumentation and Database with a Complete Healthcare Technology Suite: MediCAN. Joint Workshop on High Confidence Medical Devices, Software, and Systems and Medical Device Plug-and-Play Interoperability. 2007:122-129.
Montgomery et al., Lifeguard—A Personal Physiological Monitor for Extreme Environments. Conf Proc IEEE Eng Med Biol Soc. 2004;3:2192-2195.
Thongpithoonrat et al., Networking and Plug-and-Play of Bedside Medical Instruments. Conf Proc IEEE Eng Med Biol Soc. 2008;2008:1514-1517.
Yang et al., Research on Multi-Parameter Physiological Monitor Based on CAN Bus. IFMBE Proceed. 2008;19:417-419.
Zeltwanger, Controller Area Network and CANopen in Medical Equipment. Bus Briefing: Med Dev Manuf Technol. 2002:34-37.
Zitzmann and Schumann, Interoperable Medical Devices Due to Standardized CANopen Interfaces. Joint Workshop on High Confidence Medical Devices, Software, and Systems and Medical Device Plug-and-Play Interoperability. 2007:97-103.
Non Final Office Action issued by the United States Patent and Trademark Office in U.S. Appl. No. 13/432,976 dated Dec. 14, 2012.
Final Rejection issued by the United States Patent and Trademark Office in U.S. Appl. No. 12/762,733 dated Dec. 20, 2012.
Final Rejection issued by the United States Patent and Trademark Office in U.S. Appl. No. 12/762,846 dated Dec. 20, 2012.

(56) References Cited

OTHER PUBLICATIONS

Final Rejection issued by the United States Patent and Trademark Office in U.S. Appl. No. 12/650,392 dated Jan. 3, 2013.
Final Rejection issued by the United States Patent and Trademark Office in U.S. Appl. No. 12/487,283 dated Jan. 3, 2013.
Non Final Office Action issued by the United States Patent and Trademark Office in U.S. Appl. No. 13/292,923 dated Jan. 14, 2013.
Notice of Allowance issued by the United States Patent and Trademark Office in U.S. Appl. No. 11/470,708 dated Jan. 18, 2013.
International Search Report and Written Opinion issued in PCT/US2012/064302 dated Jan. 15, 2013.

* cited by examiner

OPTICAL SENSOR FOR MEASURING PHYSIOLOGICAL PROPERTIES

RELATED APPLICATIONS

The present application claims the benefit of priority to U.S. Provisional Application No. 61/444,320, filed Feb. 18, 2011, which is hereby incorporated by reference, including the drawings.

BACKGROUND OF THE INVENTION

The following discussion of the background of the invention is merely provided to aid the reader in understanding the invention and is not admitted to describe or constitute prior art to the present invention.

The saturation of peripheral oxygen in the blood (SpO2) is sometimes referred to as the 'fifth vital sign'. Medical professionals can detect hypoxemia, i.e. a deficiency of oxygen, by monitoring a patient's SpO2. Values between about 95-100% are considered normal; those below this indicate hypoxemia, and will typically trigger an alarm in a hospital setting.

A technique called pulse oximetry measures SpO2. Technically this parameter is determined from a patient's arterial oxygen saturation, or SaO2, which is a percentage of oxygenated arterial hemoglobin present in their blood. Functional hemoglobin molecules can bind with up to four oxygen molecules to yield 'oxygenated' hemoglobin (HbO2). A hemoglobin molecule bound to less than four oxygen molecules is classified as 'reduced' hemoglobin (Hb). Conventional pulse oximeters feature algorithms that assume only HbO2 and Hb are present in the blood, and measure SpO2 from the ratio of oxygenated hemoglobin to the total amount of hemoglobin (both oxygenated and reduced) according to equation (1):

$$SpO2 = \frac{HbO2}{HbO2 + Hb} \tag{1}$$

HbO2 and Hb feature different absorption spectra in the visible and infrared regions, and can therefore be measured optically. Conventional pulse oximeters thus typically feature light sources (most typically light-emitting diodes, or LEDs) that radiate in the red (near 660 nm) and infrared (typically between 900-950 nm) spectral regions. A photodetector measures a portion of radiation at each wavelength that transmits through the patient's pulsating blood, but is not absorbed. At 660 nm, for example, Hb absorbs about ten times as much radiation as HbO2, whereas at 905 nm HbO2 absorbs about two times as much radiation as Hb. Detection of transmitted radiation at these wavelengths yields two time-dependent waveforms, each called a plethysmogram (PPG), that an oximeter analyzes to solve for SpO2 as defined in equation (1) above.

Specifically, the oximeter processes PPG waveforms measured with red (RED(PPG)) and infrared (IR(PPG)) wavelengths to determine time-dependent AC and DC signals. The term 'AC' signals, as used herein, refers to a portion of a PPG waveform that varies relatively rapidly with time, e.g. the portion of the signal modulated by pulsations in the patient's blood. 'DC' signals, in contrast, are portions of the PPG that are relatively invariant with time, e.g. the portion of the signal originating from scattering off of components such as bone, skin, and non-pulsating components of the patient's blood.

More specifically, AC signals are modulated by a heartbeat-induced pulse present in both waveforms. The pulse represents a pressure wave, launched by the heart, which propagates through the patient's vasculature and causes a time-dependent increase in volume in both arteries and capillaries. When the pressure pulse reaches vasculature irradiated by the oximeter's optical system, a temporary volumetric increase results in a relatively large optical absorption according to the Beer-Lambert Law. Typically only about 0.5-1% of the total signal measured by the photodetector originates from the AC signal, with the remainder originating from the DC signal. Separation of AC and DC signals is typically done with both analog and digital filtering techniques that are well-known in the art.

During pulse oximetry a normalized 'r' value is typically calculated from AC and DC signals using equation (2), below:

$$r = \frac{660 \text{ nm(AC)}/660 \text{ nm(DC)}}{905 \text{ nm(AC)}/905 \text{ nm(DC)}} \tag{2}$$

r, which is sometimes called a 'ratio of ratios' (RoR), represents a ratio of Hb to HbO2. It equates an actual SpO2 value, which ranges from 0-100% O2, to an empirical relationship that resembles a non-linear equation. Above about 70% O2 this equation typically yields values that are accurate to a few percent. Measurements below this value, while not necessarily accurate, still indicate a hypoxic patient in need of medical attention.

Like SpO2, continuous noninvasive blood pressure ("cNIBP") monitoring relies on accurate measurement of PPG and ACC waveforms obtained from a pulse oximeter, together with an electrocardiogram waveform (ECG). cNIBP is typically measured with the 'Composite Technique', which is described in detail in the co-pending patent applications entitled: VITAL SIGN MONITOR FOR MEASURING BLOOD PRESSURE USING OPTICAL, ELECTRICAL, AND PRESSURE WAVEFORMS (U.S. Ser. No. 12/138,194; filed Jun. 12, 2008 and published as 20090018453A1), and BODY-WORN SYSTEM FOR MEASURING CONTINUOUS NON-INVASIVE BLOOD PRESSURE (cNIBP) (U.S. Ser. No. 12/650,354, filed Nov. 15, 2009 and published as 20100168589A1), the contents of which are fully incorporated herein by reference.

As described therein, the Composite Technique (or, alternatively, the 'Hybrid Technique' referred to therein) typically uses a single PPG waveform from the SpO2 measurement (typically the IR(PPG) waveform, as this typically has a better signal-to-noise ratio than the RED(PPG) waveform), along with the ECG waveform, to calculate a parameter called 'pulse transit time' (PTT) which strongly correlates to blood pressure. Specifically, the ECG waveform features a sharply peaked QRS complex that indicates depolarization of the heart's left ventricle, and, informally, provides a time-dependent marker of a heart beat. PTT is the time separating the peak of the QRS complex and the onset, or 'foot', of the RED/IR(PPG) waveforms; it is typically a few hundred milliseconds. The QRS complex, along with the foot of each pulse in the RED/IR(PPG), can be used to more accurately extract AC signals using a mathematical technique described in detail below. In certain embodiments, both the RED/IR(PPG) waveforms may be collectively processed to enhance the accuracy of the cNIBP measurement.

Typical pulse oximeters feature a probe encased in a clothespin-shaped housing that includes both red and infrared LEDs, and a photodetector that detects radiation from the LEDs after it passes through a portion of the patient's body. The probe typically clips to a patient's index finger. Most probes operate in a transmission-mode optical geometry, and relay analog waveforms measured by LEDs and the photodetector to an external processing unit. Because it is based on an optical measurement, pulse oximetry can be extremely sensitive to a patient's motion. Activities such as walking, finger tapping, falling, and convulsing can result in a number of artifacts that distort both the AC and DC components of waveforms measured with the oximeter's optical system. Motion-related activities, for example, can cause the oximeter probe to move relative to the patient's finger, change the amount of ambient light that irradiates the photodetector, and disrupt both arterial and venus blood flow in vasculature measured by the optical system. Each of these events can generate artifacts that, in some cases, are similar to the AC and DC signals within the PPG waveforms. Ultimately this can cause the pulse oximeter to generate inaccurate values and false alarms.

International Patent Application No. PCT/US2010/039000, which is hereby incorporated by reference in its entirety, describes a physiological probe that comfortably clips to the base of the patient's thumb, thereby freeing up their fingers for conventional activities in a hospital, such as reading and eating. The probe reversibly secures to the thumb with, e.g., an easy-to-use Velcro strap, disposable tape, or similar closure, or may be provided in the form of a closed ring which slips over the thumb. It measures time-dependent waveforms (RED/IR(PPG)) corresponding to LEDs typically operating near 660 nm and 905 nm. Clinically accurate pulse oximetry measurements made at the base of the patient's thumb require a set of coefficients relating r (from Eq. 2) to SpO2 that are typically determined with a set of empirical experiments (e.g. a 'breathe down' study, described below). These coefficients differ from those used in conventional oximetry measurements because of the differences between vasculature in the base of the thumb and the tip of the index finger. Typically the base of the thumb features relatively fewer capillary beds, and thus the coefficients are preferably adjusted accordingly.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

SUMMARY OF THE INVENTION

It is an object of the present invention to provide a physiological probe having at least one emitter and an associated detector configured to attach to a tissue site, where the detector is configured to measure a detector signal responsive to the intensity of energy from the emitter after it has interacted with a tissue site. These physiological probes, which are well suited to function as pulse oximeter probes as described hereinafter, are configured for securing to a digit of the subject, and most preferably to a subject's thumb at the level of a proximal phalanx.

In particular, the physiological probe of the present invention comprises a sensor module and a cradle module. In various aspects, the present invention relates to the individual components of the probe, to the probe itself, and to methods of its manufacture and use.

The sensor module comprises: (a) a electronic circuitry, which in certain embodiments takes the form of a flexible circuit board, which comprises (i) one or more, and preferably at least two sources of electromagnetic radiation, and (ii) a photodetector configured to detect the radiation from the source(s) which has passed through or been reflected by the subject's tissue, thereby acquiring data relating to at least the oxygen saturation level of blood of the subject, wherein the photodetector is operably connected to a connection cable for delivery of photodetector signals to an external processing unit; and (b) a flexible enclosure providing a cover for the circuit board, wherein the flexible enclosure comprises (i) at least one aperture through which the source(s) emit radiation for irradiating the subject's tissue, (ii) at least one aperture through which the photodetector receives radiation which has interacted with (e.g., passed through and/or been reflected by) the subject's tissue, and (iii) an aperture through which the connection cable passes.

The cradle module comprises: at least first and second rigid housing members mated to one another via a hinge region to form an approximately semicircular ring which is configured to reversibly receive the sensor module; that is, in use the sensor module is releasably attached to the cradle module.

Optionally, the physiological probe of the present invention further comprises a retainer attached to the cradle module and configured to reversibly attach the physiological probe to the digit of the subject, for example by wrapping around the entire circumference of the digit.

As used herein, the term "releasably attached" refers to two separate modules which may be engaged with and disengaged from one another in the course of normal use. In certain embodiments, the hinge region is configured to provide a range of adjustment in the diameter of the ring while physically constraining the included angle measured between the sources and the photodetector within a predetermined range. As used herein, the term "semicircular ring" is not meant to refer to the geometric shape forming an arc of constant radius extending through 180 degrees. Rather, the term refers to a shape which fits circumferentially around a portion of, but not the complete circumference of, a digit as depicted, for example, in FIG. 4.

As noted, the hinge region provides a range of adjustment in the diameter of the semicircular ring formed by the cradle, thereby allowing the physiological probe to adjust to a range of different digit girths. In certain embodiments meant to be compatible with the human thumb, the hinge of an adult-sized cradle is preferably designed to accommodate a girth of between about 6.2 cm and about 7.4 cm, with pediatric sizes or sizes for other (smaller) digits being made appropriately smaller. At the same time, it is important for proper functioning that the geometry of the radiation sources and the photodetector be maintained within an acceptable range for proper function of the sensor.

In one example, the hinge region may be a pivoting joint in which a pin on one rigid housing member fits into a corresponding hole on the other rigid housing member. Alternatively, the hinge region may simply be a flexible region which bridges the two rigid housing members. Other types of hinge arrangements will be apparent to the skilled artisan. When desired, the angular constraint can be accomplished by providing "stops" in one or both of the first and second rigid housing members which prevent opening or closing of the hinge past the predetermined range. Preferably, the predetermined range of the included angle measured between the sources and the photodetector are less than or equal to about 60°, and more preferably between about 60° and about 30°, and most preferably between about 55° and about 35°. The term "about" in the context of this patent application refers to +/−10% of a given measurement.

The cradle module is preferably designed as a disposable component which receives a sensor module preferably designed for multiple uses. As used herein, the term "disposable" with regard to the cradle refers to the characteristic that the cradle module may be disengaged from sensor module in the course of normal use by the user of the physiological probe such that the sensor module may be easily separated from, and need not be discarded with, the cradle. This can serve to place the device components of the physiological probe most susceptible to wear and cleanability issues on a disposable unit, while retaining the more expensive electronic components on an easily cleanable and reusable unit. In certain embodiments, the hinge is configured such that a force may be applied to move the hinge past one or more of its "stops," thereby separating the first and second rigid housing members and preventing improper reuse. This can also facilitate removal of the sensor module for its reuse. In certain embodiments, the sensor module can be rendered cleanable for reuse by sealing of the apertures positioned proximal to the radiation source(s) and the detector with a material providing sufficient transparency to the appropriate wavelengths being employed in the device.

When the sensor module is mated to the cradle, the sensor module substantially conforms to the semicircular ring shape created by the cradle. As used herein, the term "substantially conforms" refers to a module which fits into the designed shape of another module in a manner which permits the two modules to function as a unit in the intended fashion. To facilitate this conformal fit, the sensor module may comprise one or more flexible hinge regions, (e.g., one or more living hinges molded into the flexible enclosure).

In certain embodiments, the surface of the sensor module and the surface of the cradle module which come into contact when the two modules are mated comprise corresponding registration structures, e.g., a ridge structure on one module which inserts into a corresponding dimple structure on the other module; a tab on one module which fits into a corresponding slot on the other module. The term "registration" as used herein refers to the act of adjusting or aligning the parts of a device in relation to each other. These corresponding registration structures can help to ensure proper placement of the sensor module into the cradle module. The combination of a rigid cradle housing and careful registration of components helps to maintain a consistent orientation of the optical components in the probe and improves the consistency of the optical path through the artery and capillary tissue, while maintaining comfort through the use of relatively soft and flexible materials on the sensor module.

In preferred embodiments, the sensor module comprises at least two flexible hinge points, such that mating of the sensor module to the cradle creates three substantially planar sensor module surfaces. A first planar surface comprises the radiation sources; a middle planar surface provides a flat base surface to engage the thumb tissue of the subject; and a third planar surface comprises the photodetector. These substantially planar surfaces can serve to improve pressure application to the underlying arteries, thereby helping to increase signal amplitudes and maintain a consistent light path.

In certain embodiments, the length of the cradle module is less than the average length of the desired proximal phalanx. In the case of an adult-sized thumb, the cradle may be about 1 cm to 1.5 cm in length, with pediatric sizes being made appropriately smaller. The term "about" in this context refers to +/−10% of a given measurement.

The radiation sources preferably emit radiation at about 660 nm and about 905 nm wavelengths. Preferably, the radiation sources are proximal to one another, and most preferably contained within the same electronic package. In proper use, the physiological probe is placed on the palmar aspect of the digit, preferably the thumb. The present invention can provide a consistent optical path from the radiation sources, through the princeps pollicis artery and soft tissue below the proximal phalanx, and subsequently to the photodetector.

Still other embodiments are found in the following detailed description of the invention, and in the claims.

DETAILED DESCRIPTION OF THE INVENTION

Figure 1:
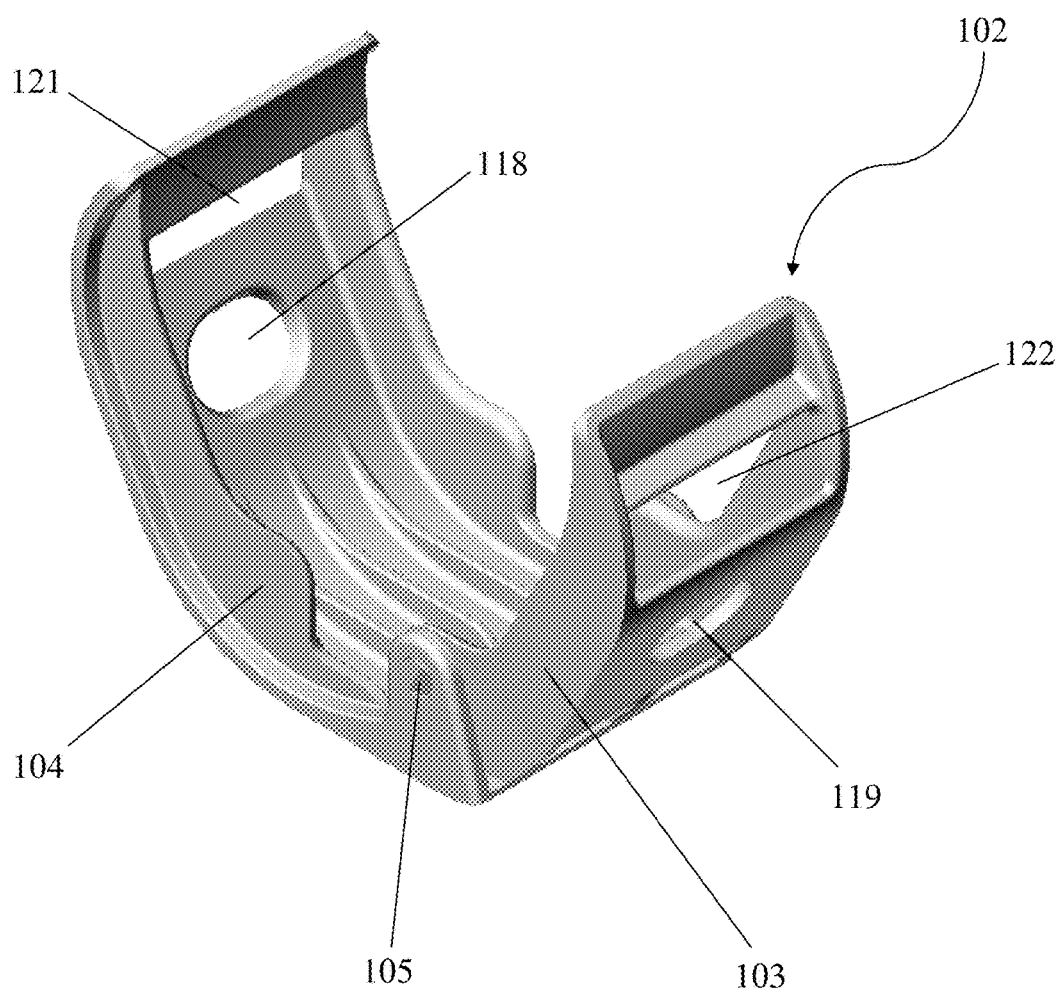
FIG. 1 shows a three-dimensional mechanical drawing of an exemplary cradle module for use as a component of a physiological probe, designed to function as a pulse oximeter probe, of the present invention.
Figure 2:
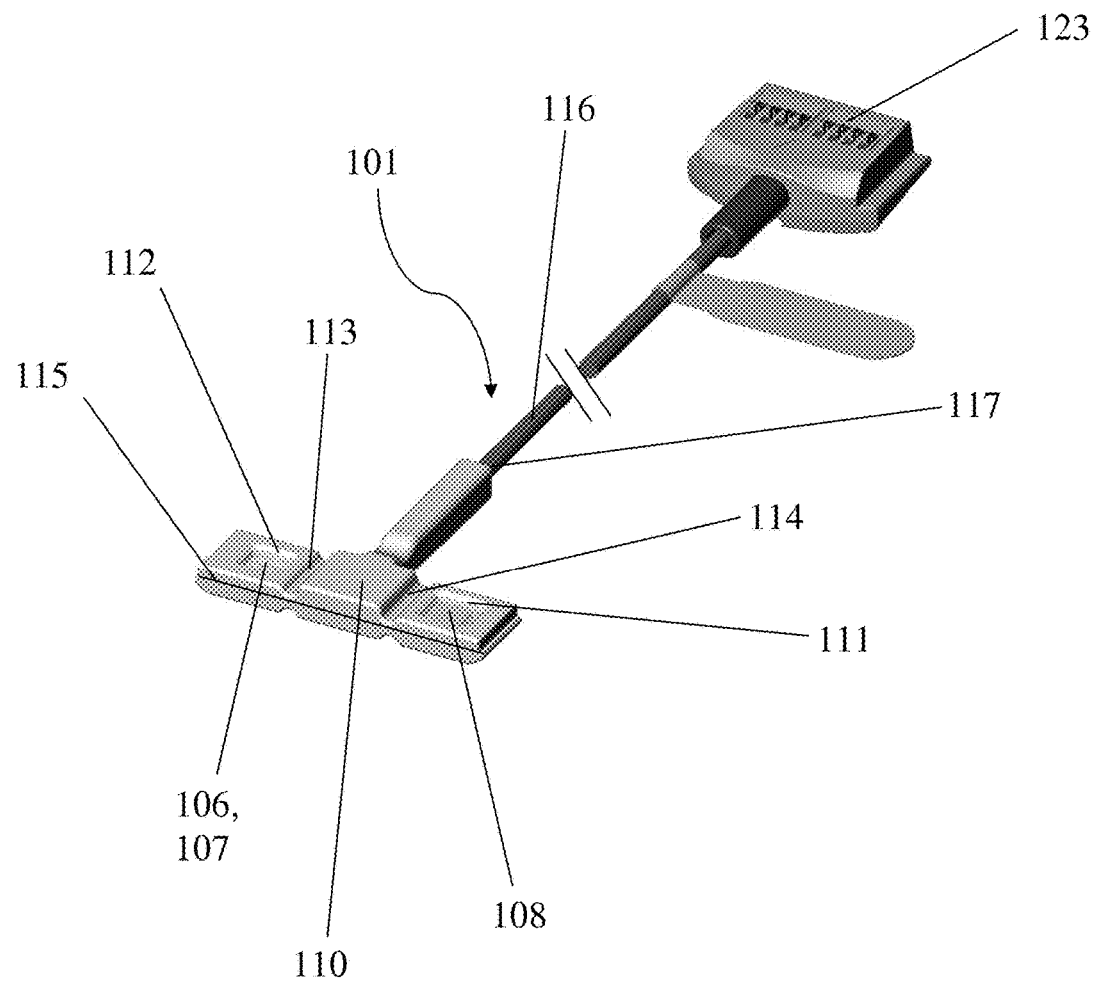
FIG. 2 shows a three-dimensional mechanical drawing of an exemplary sensor module for use as a component of a physiological probe, designed to function as a pulse oximeter probe, of the present invention.
Figure 3:
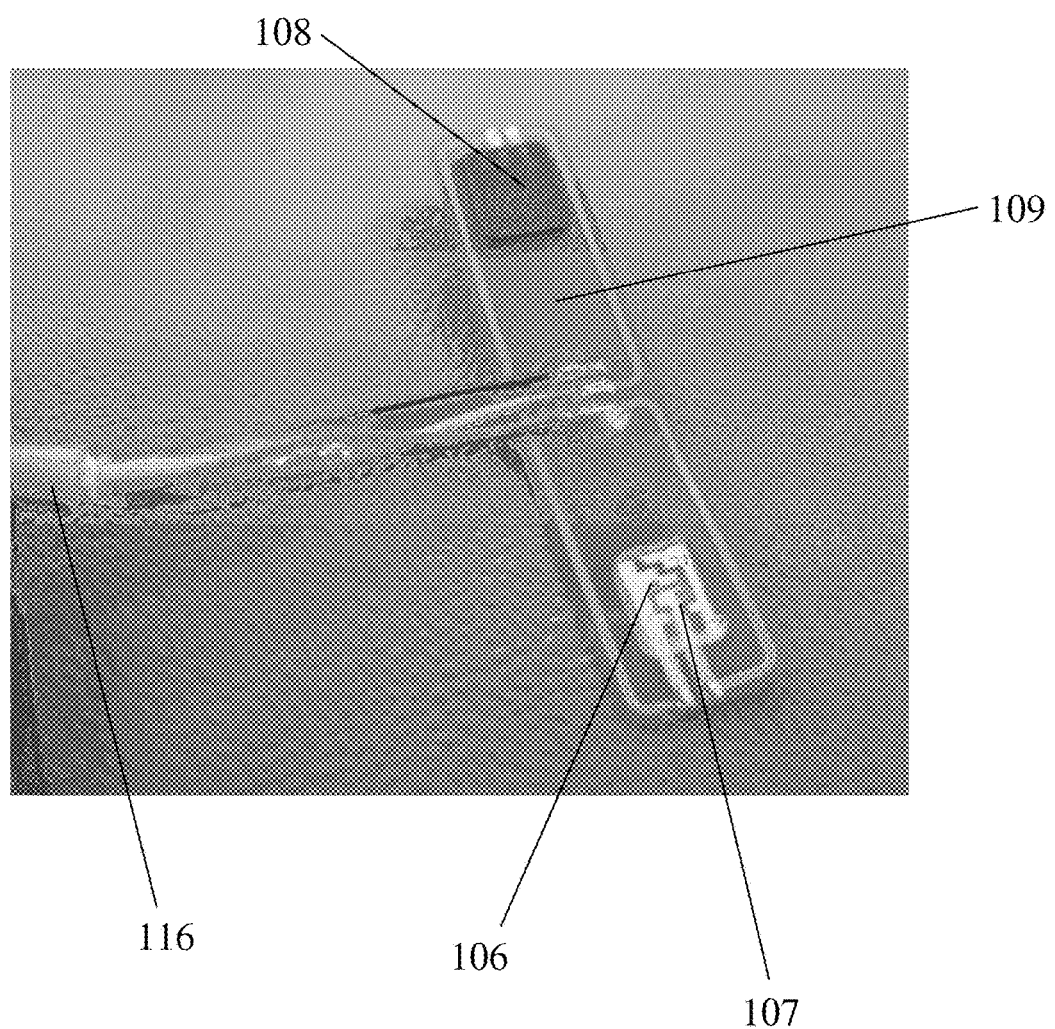
FIG. 3 shows a photograph of a distal end of the sensor module of FIG. 2 which includes a pair of light sources and a photodetector.

FIGS. 1-4 depict components of a semicircular physiologic probe 100 comprising a separate sensor module 101 and cradle module 102 which mate to one another. The probe is designed to be comfortably worn for extended periods (e.g. several days) while freeing up the patient's fingers for activities such as reading and eating that are commonplace in, e.g., a hospital. While described in detail as a pulse oximeter probe, the physiological probes of the present invention are applicable to any similar device having at least one emitter and an associated detector configured to attach to a tissue site.

The cradle module 102 is shaped as a semicircular ring that wraps around a base of patient's digit to measure time-dependent waveforms (PPG) that can be used, e.g., in the determination of SpO2 and cNIBP. The cradle module 102 is comprised of two substantially rigid members 103, 104 connected by a hinge 105. The rigid members 103, 104 may be made out of a number of materials known in the art such as plastics, metals, and the like; for example, polypropylene, acrylates (PMMA, SMMA, etc.), styrenes (SAN, PS, ASA, ABS, etc.), polycarbonate, copolymers, ionomer resins (Surlyn), polyamides, polyesters, thermoplastic elastomers, aluminum, brass, nickel, etc. A preferred example is Eastman Tritan™ copolyester. The length of the cradle module is less than the average length of the proximal phalanx so as not to interfere with bending of the digit at the joint. An optimal length for an adult-sized cradle configured for attachment to a thumb is in the range of 1 cm to 1.5 cm.

Figure 4A:
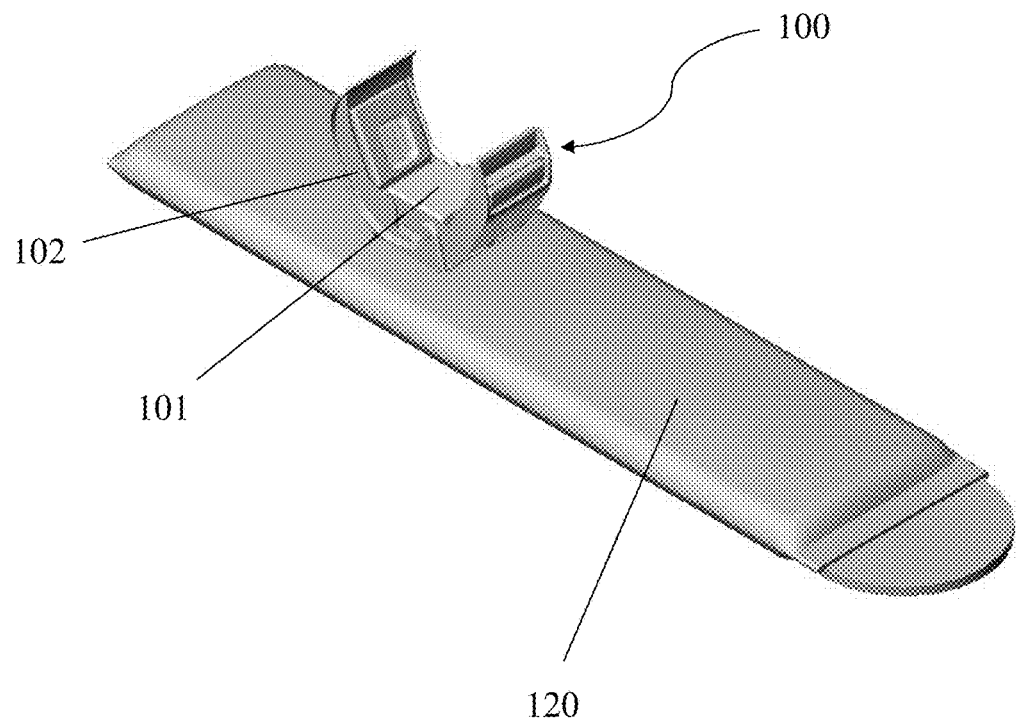
FIGS. 4A-B show three-dimensional mechanical drawings of the cradle module of FIG. 1 attached to a flexible material configured to wrap around a patient's thumb and housing the sensor module of FIG. 2.
Figure 4B:
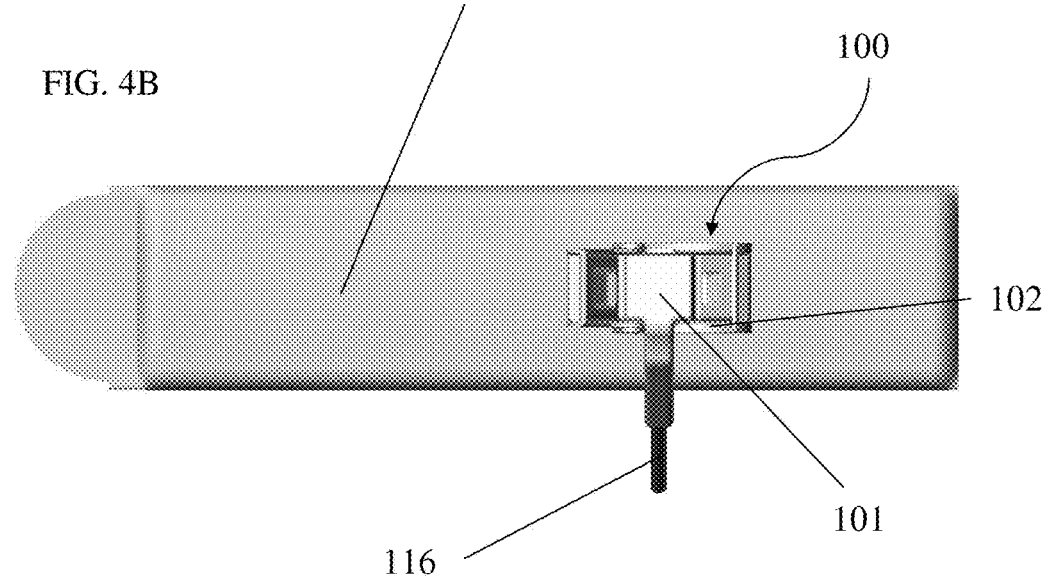
Figure 4C:
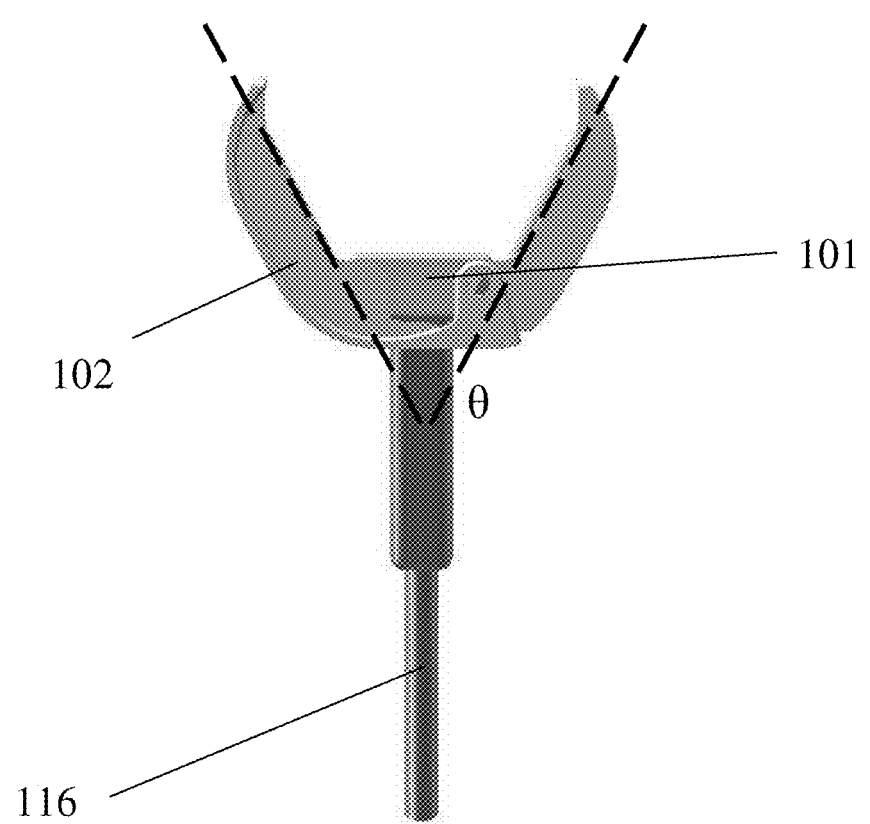
FIG. 4C shows a two-dimensional mechanical drawing of the cradle module of FIG. 1 housing the sensor module of FIG. 2.

A portion of each rigid member lying below the hinge location by providing points of interfering physical contact between the two rigid members which act as stops to constrain the opening and closing of the hinge within a predetermined range. This serves two purposes. First, the hinge 105 provides a range of adjustment in the diameter of the opening in the semicircular ring which fits over the digit, thereby allowing the physiological probe to adjust to a range of different finger sizes. In certain embodiments, the hinge of an adult-sized cradle is preferably designed to accommodate a thumb diameter of about 1.8-2.3 cm, or a girth of between about 6.2 cm and about 7.4 cm. Second, to increase the amount of radiation that passes through the artery and capillaries in the tissue, and thereby optimize signal quality, the cradle acts to maintain the LEDs 106, 107 and photodiode 108 at an included angle (θ) of approximately 35-55 degrees. As shown in FIG. 4C, the 'included angle θ' refers to the angle formed between a first line drawn parallel to the planar surface comprising the radiation source and a second line drawn parallel to the planar surface comprising the photodetector. Optical components separated at this angle tend to increase the relative contribution of signal coming from the artery; ultimately this improves the accuracy of the cNIBP measurement, as PTT values measured from arterial components correlate better to blood pressure than those measured from capillary components.

The probe makes a transmission-mode optical measurement along an inner portion of the digit with the pair of embedded LEDs 106, 107 operating at, respectively, 660 and 905 nm, and a single photodetector 108 that detects these wavelengths after they pass through vasculature and other tissue lying beneath the LEDs. Preferably, both LEDs and the photodetector are positioned to measure blood pulsing in portions of the princeps pollicis artery, which is the principal artery of the thumb and stems from the radial artery. Measuring blood flowing in this artery enhances the accuracy of a PTT-based measurements of blood pressure, as is described in more detail in VITAL SIGN MONITOR FOR MEASURING BLOOD PRESSURE USING OPTICAL, ELECTRICAL, AND PRESSURE WAVEFORMS (U.S. Ser. No. 12/138,194; filed Jun. 12, 2008 and published as 20090018453A1), and BODY-WORN SYSTEM FOR MEASURING CONTINUOUS NON-INVASIVE BLOOD PRESSURE (cNIBP) (U.S. Ser. No. 12/650,354, filed Nov. 15, 2009 and published as 20100168589A1), the contents of which have been previously incorporated by reference.

Electronic circuitry providing the LEDs and photodetector may be provided in the form of a small flexible circuit board 109 in the sensor module, which may additionally include, for example, a trans-impedance amplifier for amplifying photocurrent from the photodetector and converting it into a corresponding voltage. The electronic circuitry can also include a resistor that identifies specific wavelengths emitted by the LEDs; these wavelengths, in turn, influence values of correlation coefficients that relate RoR to SpO2, as described below. In other embodiments, the flexible circuit board 109 can be replaced with a series of insulated wires that connect the LEDs, photodetector, trans-impedance amplifier, and other components to form a circuit.

A flexible housing 110 covers and protects the flexible circuit board 109. The flexible housing 110 may preferably be formed from any water and alcohol-resistant material, with materials having a durometer (A) in the range of 25 to 60 (e.g., HTV, RTV, or LSR elastomers, etc.) providing an optimum combination of comfort and sufficient resistance to compression to allow the probe to apply pressure to the underlying arteries. A particularly preferred material has a durometer (A) of about 40, such as Nusil MED-4044 silicone elastomer. For purposes of manufacturing, the circuit board may be inserted into the housing through a slit-like opening 115 at the top, which may then be sealed, for example with a liquid silicone elastomeric material. A connection cable 116 extends through an opening 117 at the bottom of the housing.

The housing features rectangular openings 111 and 112 through which the LEDs emit, and the photodetector receives, radiation. In certain embodiments a filter may be provided over the photodetector in order to both seal the aperture and filter undesired ambient light frequencies. On the emission side, the opening 11 may be sealed using a silicone material which is sufficiently transparent at the emission wavelengths. Forming the housing in a white color allows the housing material to reflect more of the scattered radiation from the sources to the detector, thereby improving sensor efficiency. The size of openings 111 and 112 also affect the efficiency of the sensor, with the optimal size being windows that are somewhat larger than the active component areas. Preferred window sizes are from about 3 to 5 mm, and may be of any shape including square, rectangular, or circular.

The housing also features two cut-out portions 113, 114, or 'living hinges', that make it easily bendable and able to accommodate to the shape of the cradle module. These living hinges serve to subdivide the cradle into three substantially planar sensor module surfaces. A first planar surface comprises the radiation sources; a middle planar surface provides a flat base surface to engage the thumb tissue of the subject; and a third planar surface comprises the photodetector. As shown in FIG. 4, when mated to the cradle, the housing substantially conforms to the shape of the cradle, while providing three relatively planar surfaces which contact the tissue. These surfaces provide for a more uniform pressure application to the underlying arteries, thereby helping to increase signal amplitudes and maintain a consistent light path. This also serves to improve sensor efficiency.

To ensure proper registration of the sensor module within the cradle module, the surfaces of each which come into contact when mated comprise corresponding registration structures, e.g., a ridge structure on the sensor module which inserts into a corresponding dimple or opening 118, 119 on the cradle module. The registration structures may take the form of a protruding ridge disposed on a surface of the sensor module housing which opposes the openings 111, 112. When the sensor module is properly positioned, the ridges insert into the openings 118, 119 in the cradle module to provide positive registration of the two modules. The skilled artisan will understand that other arrangements of registration structures may be probided. For example, the protruding ridge may be disposed on a surface of the cradle module, and a corresponding dimple may be disposed on the sensor module. The distal portions of the sensor module may also insert into registration slots 121, 122 in the cradle module, thereby further ensuring proper positioning of the sensor module within this component.

The probe is held in place around the base of the digit with a reclosable retainer, such as a flexible nylon strap 120. The strap can be attached to the cradle in a number of methods known in the art, such as threading through two openings located the cradle's distal ends; or by bonding of the cradle to the strap via an adhesive, heat-staking or ultra-sonic welding as depicted in FIG. 4. A portion of the strap features a patch of Velcro (containing, e.g., 'hooks') that adheres to a mated patch (containing, e.g., 'loops') on the strap's main portion; the patches reversibly adhere to each other when the probe is placed on the patient's digit, and easily detach so that it can be removed. The strap allows the probe to be securely fastened, which in turn minimizes motion relative to the measurement site.

The flexible cable 116 serves to connect the electronics of the oximeter probe to an external processor for processing signals necessary to determine SpO2 and/or blood pressure measurements. The cable can carry I/O signals to the probe electronics that drive the LEDs according to a timing diagram, and analog signals measured by the photodetector to an amplifying/filtering circuit. The cable preferably comprises a distal connector 123 that plugs into an external processing module to operably connect the probe to an external processor. There, the analog signals are amplified, filtered, digitized, and processed to measure SpO2 and/or blood pressure (e.g. cNIBP) values, as described in detail below.

A detailed description of a preferred embodiment for the circuitry to be incorporated into the oximeter probe, and interconnection of the oximeter probe to a wrist-worn external processing module may be found in International Patent Application No. PCT/US2010/039000 entitled BODY-WORN PULSE OXIMETER, which is hereby incorporated by reference in its entirety.

Figure 5:
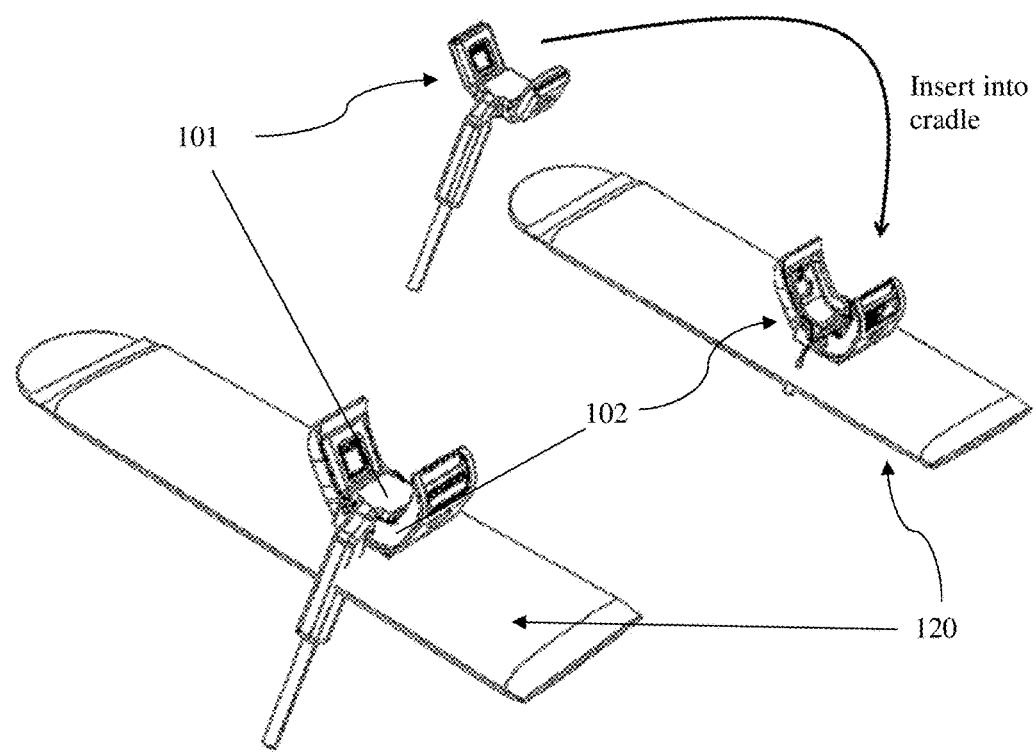
FIG. 5 is a series of mechanical drawings depicting how the sensor module of FIG. 2 inserts into the cradle module of FIG. 1 to form an exemplary physiological probe.

FIG. 5 depicts in schematic form one example of the sensor module being inserted into the cradle module prior to use. For insertion, the sensor module is flexed at living hinges so that it may approximate the semicircular shape of the cradle module. As noted above with regard to FIG. 2, the sensor module contains the electronic components of the physiological probe, and is configured for multiple uses. In contrast, as depicted in FIG. 1, the cradle lacks electronic components and is intended for disposable use as it contains parts which may be more difficult to properly clean. Because of the rigid structure and constrained hinge of the cradle module, insertion of the sensor module into the cradle module serves to properly position the LEDs relative to the photodetector for an accurate pulse oximetry measurement.

During a pulse oximetry measurement the LEDs intermittently emit beams of radiation at 660 nm and 905 nm at roughly 500 Hz according. Once emitted, the beams pass into the underlying tissue and rapidly diverge to scatter off tissue such as skin, bone, and capillaries near the tissue's outer surface. In the case of the thumb, a portion of the princeps pollicis artery is also sampled by the radiation before it illuminates the photodetector. Both the capillaries and the arteries carry blood that pulsates with each heartbeat and absorbs radiation emitted by the LEDs. This results in separate time-dependent optical waveforms (i.e. RED/IR (PPG), generated by the 660 and 905 nm radiation. Both waveforms feature AC signals corresponding to the time-dependent pulsating blood, and DC signals corresponding to time-independent scattering off the skin, bone, and non-pulsating components of the capillaries and artery. Prior to any filtering the AC component typically represents about 0.5-1% of the total signal.

Collectively processing both the AC and DC signals of the RED/IR(PPG) waveforms yields a SpO2 value. The external processor can calculate these components using a number of signal-processing methodologies that are additionally important for determining PTT-based cNIBP. Ultimately the AC and DC components yield a RoR which then relates to a SpO2 using a series of empirically determined coefficients. In one embodiment, for example, the RoR is determined by first measuring RED/IR(PPG) waveforms, and then passing them through a low-pass filter characterized by a 20 Hz cutoff. The averaged baseline components of each waveform are sampled and stored in memory, and represent RED/IR (DC). Both waveforms are then additionally filtered with high-pass filter having a 0.1 Hz cutoff frequency, which is typically implemented with a finite impulse response function, and finally amplified with a variable gain amplifier. These steps can be done with either analog electronic or digital software filters. Once determined, the AC and DC signals are processed to yield a RoR value, described in equation (3), which relates to SpO2:

$$RoR = \frac{RED(AC)/RED(DC)}{IR(AC)/IR(DC)} \quad (3)$$

Figure 6:
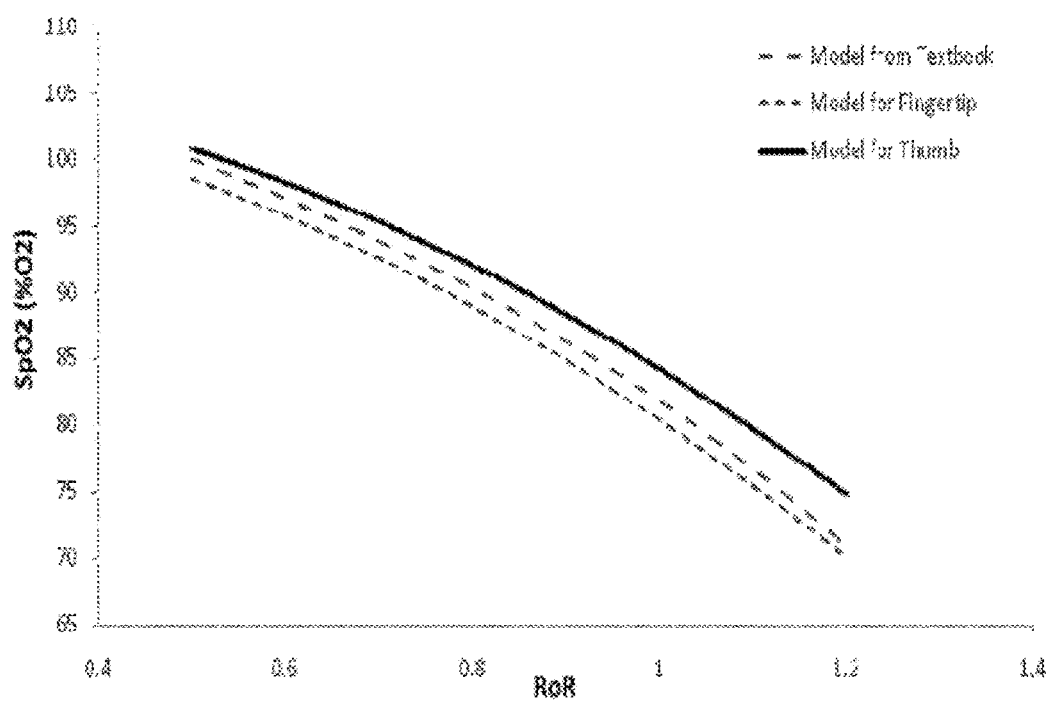
FIG. 6 shows a graph depicting a relationship between SpO2 and a 'ratio of ratios' (RoR) for measurements from theoretical model in a medical textbook, made from the tip of a patient's index finger, and made from the base of a patient's thumb.

FIG. 6 shows an empirical relationship between RoR and SpO2 for measurements made at the base of the thumb with the oximeter probe, along with similar relationships for measurements made at the tip of the index finger with an off-the-shelf oximeter probe (small dashes), and the theoretical curve for measurements made from the tip of the index finger (large dashes). Curves corresponding to measurements made from the index finger and thumb are determined empirically from a group of patients measured under similar conditions. As is clear from the figure, the relationships between RoR and SpO2 are similar, but slightly offset due to differences in the measurement site. Without being bound to any theory, these differences may be due to the relatively low density of capillary beds near the base of the thumb as compared to those in the tip of the index finger. The relationship for all curves in FIG. 6 is non-linear, particularly for SpO2 values ranging from about 70-100%. Values below 70% can be accounted for with a different non-linear model, such as one based on a second-order polynomial. Coefficients a, b, and c for this model are determined by fitting the empirical data to a corresponding mathematical function like the second-order polynomial shown in equation (4) below:

$$SpO2 = (a + b*RoR + c*RoR^2) \times 100 \quad (4)$$

Optimized values for a, b, and c coefficients corresponding to measurements made at the base of the thumb are shown in Table 1, below:

TABLE 1 coefficients for equation 4 relating RoR to SpO2 for measurements made at the base of the thumb

| Parameter | Value |
|---|---|
| A | 107.3 |
| B | −3.0 |
| C | −20.0 |

The exact values of parameters shown in Table 1 will depend of the specific wavelengths of the LEDs used in the pulse oximeter probe. This is because the SpO2 measurement is fundamentally determined by the relative optical absorption of Hb and HbO2 in the red and infrared spectral regions, and absorption, in turn, will depend on the wavelength emitted by the LEDs. The absorption spectra of Hb and HbO2 are relatively flat in the infrared spectral region, but strongly diverge in the red spectral region. The coefficients shown in Table 1 are thus relatively sensitive to the exact wavelength of the red LED. For this reason, a series of empirical studies need to be performed using pulse oximeter probes featuring LEDs of varying wavelengths surrounding the red emission wavelength (e.g. 600-610 nm) prior to manufacturing. Such a study is typically classified as a 'breathe down' study because it involves lowering the SpO2 values of a series of patients (typically about 10-15) under medical supervision. SpO2 is typically lowered by decreasing the amount of oxygen each patient inhales through a specialized ventilator mask; this is often done in a room with a reduced temperature. Blood from the patients is extracted from an arterial line and analyzed with a blood gas analyzer to determine its oxygen content. Simultaneously, a pulse oximeter probe with known LED wavelengths is attached to each patient (in this case at the base of the thumb) and used to measure the RoR described in equation (3). SpO2 values for this experiment, as measured with the blood gas analyzer, typically range from 70-100%. Simultaneous studies are typically done using pulse oximeter probes having LEDs with different red emission spectra. Upon completion of the studies, the wavelength-dependent values of RoR are related to SpO2, as determined by the blood gas analyzer, to calculate coefficients a, b, c as described in Table 1. In general, a different set of coefficients will result for the different LED wavelengths. These coefficients and the optical wavelengths they correspond to, along with a resistor value described below, are stored in a database in memory on the wrist-worn transceiver.

Measurements made at the base of the thumb provide improvements to the measurement of SpO2 values because the circulatory anatomy at this location yields a more predictable arterial signal; this location also increases patient comfort by freeing up the tips of the fingers for use. The IR(PPG) measured from this site, when processed in combination to the ECG waveform, yields a PTT value that can be processed with the Composite Technique to yield an accurate cNIBP measurement. As described above, an IR(PPG) waveform measured from primarily from the princeps pollicis artery increases the accuracy of the cNIBP measurement. With an initial pressure-based calibration systolic (SYS) and diastolic (DIA) blood pressure can be explicitly determined for each heartbeat using an algorithm described in the above-mentioned patent applications, the contents of which have been previously incorporated herein by reference. Typically, PTT values are processed over a 20-40 second time period (often implemented as a 'rolling average') using statistical filtering to improve accuracy. To better define the onset of the PPG waveform, and thus improve the accuracy to which SYS and DIA are determined, times corresponding to RED(foot) and IR(foot) are typically averaged together. When compared to SYS and DIA values measured under clinical conditions with a femoral arterial line, cNIBP measurements made from this particular location were well within the FDA's standards for accuracy (+/−5 mmHg) and standard deviation (8 mmHg). For this and other reasons the base of the thumb appears to be a uniquely good location for measuring both SpO2 and cNIBP.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A physiological probe configured for securing to a subject's digit, comprising:
    a sensor module comprising
        (a) electronic circuitry which comprises (i) at least one source of electromagnetic radiation, and (ii) a photodetector configured to detect radiation from the at least one source of electromagnetic radiation after it has interacted with the subject's tissue, thereby acquiring data relating to at least one physiologic property of the subject, wherein the photodetector is operably connected to a connection cable for delivery of photodetector signals to an external processing unit, and
        (b) a flexible enclosure providing a cover for the electronic circuitry, wherein the flexible enclosure comprises (i) at least one aperture through which the at least one source of electromagnetic radiation emits radiation for irradiating the subject's tissue, (ii) at least one aperture through which the photodetector receives radiation after it has interacted with the subject's tissue, and (iii) an aperture through which the connection cable passes; and a cradle module comprising
  (a) at least first and second rigid housing members mated to one another via a hinge region to form an approximately semicircular ring which is configured to releasably receive the sensor module, wherein the hinge region is configured to provide, when secured to the subject's digit, a range of adjustment in a diameter of the ring while physically constraining an included angle measured between the at least one source of electromagnetic radiation and the photodetector within a predetermined range, wherein the predetermined range of the included angle measured between the source(s) of electromagnetic radiation and the photodetector is between about 60° and about 30°.

2. A physiological probe according to claim 1, wherein the hinge is configured to accommodate a subject's thumb at the level of the proximal phalanx for purposes of acquiring the data relating to at least one physiologic property of the subject.

3. A physiological probe according to claim 1, wherein the hinge is configured to accommodate a girth of between about 6.2 cm and about 7.4 cm.

4. A physiological probe according to claim 1, wherein the hinge region is a pivoting hinge formed by mating the first and second rigid housing members, and wherein the structure of the first and second rigid housing members constrains opening or closing of the hinge beyond the predetermined range when mated to one another via the pivoting hinge.

5. A physiological probe according to claim 4, wherein, the hinge is configured such that a force applied to move the hinge beyond the predetermined range separates the first and second rigid housing members.

6. A physiological probe according to claim 1, wherein the predetermined range of the included angle measured between the source(s) of electromagnetic radiation and the photodetector is between about 55° and about 35°.

7. A physiological probe according to claim 1, wherein the sensor module comprises one or more hinge points in the flexible enclosure.

8. A physiological probe according to claim 7, wherein the sensor module comprises at least two hinge points in the flexible enclosure configured to provide three substantially planar sensor module surfaces when the sensor module is mated to the cradle module.

9. A physiological probe according to claim 1, wherein the surface of the sensor module and the surface of the cradle module which come into contact when the two modules are mated comprise corresponding registration structures configured to register the position of the sensor module in the cradle module.

10. A physiological probe according to claim 1, wherein the length of the cradle module is between about 1 cm and about 1.5 cm.

11. A physiological probe according to claim 1, wherein the cradle module is disposable.

12. A method of obtaining pulse oximetry signals from a subject, comprising:
  affixing a physiological probe according to claim 1 to the palmar aspect of a digit of the subject at the level of the proximal phalanx, wherein the probe is positioned on the subject's digit such that the source(s) of electromagnetic radiation, when energized, provide irradiation of tissues of the subject through the capillary, arterial, and soft tissue of the digit, and subsequently to the photodetector;
  energizing the sources to irradiate the tissues of the subject; and
  detecting photodetector signals at an external processing unit operably connected via the connection cable.

13. A method according to claim 12, further comprising calculating one or more of a blood pressure value, an SpO2 value, a pulse rate, a respiration cycle, and a photoplethysmograph waveform for the subject using the photodetector signals.

14. A method according to claim 12, comprising determining a blood pressure value for the subject using the photodetector signals.

* * * * *